(12) United States Patent
Klem

(10) Patent No.: US 11,906,009 B2
(45) Date of Patent: Feb. 20, 2024

(54) ROTATIONAL JOINT ASSEMBLY FOR ROBOTIC MEDICAL SYSTEM

(71) Applicant: Corindus, Inc., Newton, MA (US)

(72) Inventor: Eric Klem, Lexington, MA (US)

(73) Assignee: Corindus, Inc., Newton, MA (US)

( * ) Notice: Subject to any disclaimer, the term of this patent is extended or adjusted under 35 U.S.C. 154(b) by 0 days.

(21) Appl. No.: 17/812,508

(22) Filed: Jul. 14, 2022

(65) Prior Publication Data

US 2023/0036346 A1 Feb. 2, 2023

Related U.S. Application Data

(60) Provisional application No. 63/203,787, filed on Jul. 30, 2021.

(51) Int. Cl.
*A61B 6/10* (2006.01)
*A61B 34/30* (2016.01)
(Continued)

(52) U.S. Cl.
CPC ............ *F16D 67/02* (2013.01); *A61B 6/105* (2013.01); *B64C 13/28* (2013.01); *A61B 34/30* (2016.02); *A61B 34/70* (2016.02); *A61B 2090/508* (2016.02); *B25J 9/101* (2013.01); *B25J 9/106* (2013.01); *B25J 15/0206* (2013.01);
(Continued)

(58) Field of Classification Search
CPC ...... F16D 67/02; F16D 53/00; F16D 2127/02; F16D 2127/04; F16D 2127/06; F16D 2125/28; F16D 2125/32; F16D 2023/123; F16D 2121/14; A61B 6/105; A61B 34/80; A61B 90/50; A61B 90/37; A61B 2090/067; A61B 2090/508; A61B 34/70; B60J 17/00; B25J 17/0004; B25J 17/0241; B25J 9/101; B25J 9/106; B25J 15/0206; B25J 15/0226

See application file for complete search history.

(56) References Cited

U.S. PATENT DOCUMENTS 3,821,525 A 6/1974 Eaton et al.
5,312,338 A 5/1994 Nelson et al.
(Continued)

FOREIGN PATENT DOCUMENTS

EP 0752237 3/2000
EP 1520548 11/2006
(Continued)

OTHER PUBLICATIONS

European Search Report for Corresponding EP Application No. 22187205.4, dated Dec. 19, 2022.

*Primary Examiner* — Tinh Dang

(57) ABSTRACT

An example rotational joint assembly for a robotic medical system, the rotational joint assembly comprising at least one arm segment and a rotational joint provided at one end of the arm segment. The rotational joint is to allow the arm segment to rotate about a rotational axis. The rotational joint comprising a brake to lock rotation of the arm segment at the rotational joint and an actuator to selectively engage or disengage the brake. The actuator comprising a cam having two stable regions separated by two transition regions, the two stable regions comprising a first stable region corresponding to engagement of the brake and a second stable region corresponding to disengagement of the brake.

19 Claims, 15 Drawing Sheets

(51) Int. Cl.
*A61B 34/00* (2016.01)
*A61B 90/50* (2016.01)
*B25J 9/10* (2006.01)
*B25J 15/02* (2006.01)
*B25J 19/00* (2006.01)
*F16D 67/02* (2006.01)
*F16D 23/12* (2006.01)
*B64C 13/28* (2006.01)
*B25J 17/02* (2006.01)
*G05B 23/02* (2006.01)
*F16D 127/02* (2012.01)
*F16D 127/04* (2012.01)
*F16D 127/06* (2012.01)
*F16D 125/28* (2012.01)
*F16D 125/32* (2012.01)
*F16D 121/14* (2012.01)

(52) U.S. Cl.
CPC ........ *B25J 15/0226* (2013.01); *B25J 17/0241* (2013.01); *B25J 19/0004* (2013.01); *F16D 2023/123* (2013.01); *F16D 2121/14* (2013.01); *F16D 2125/28* (2013.01); *F16D 2125/32* (2013.01); *F16D 2127/02* (2013.01); *F16D 2127/04* (2013.01); *F16D 2127/06* (2013.01); *G05B 23/0286* (2013.01)

(56) References Cited

U.S. PATENT DOCUMENTS

| | | |
|---|---|---|
| 5,350,101 A | 9/1994 | Godlewski |
| 6,793,380 B2 | 9/2004 | Kupfer |
| 7,331,967 B2 | 2/2008 | Lee et al. |
| 7,556,626 B2 | 7/2009 | Jeda et al. |
| 7,607,183 B2 | 10/2009 | Somasundaram et al. |
| 7,766,856 B2 | 8/2010 | Ferry et al. |
| 7,766,894 B2 | 8/2010 | Weitzner et al. |
| 7,833,018 B2 | 11/2010 | Alexander et al. |
| 7,972,298 B2 | 7/2011 | Wallace et al. |
| 8,052,636 B2 | 11/2011 | Moll et al. |
| 8,092,397 B2 | 1/2012 | Wallace et al. |
| 8,343,096 B2 | 1/2013 | Kirschenman et al. |
| 8,617,102 B2 | 12/2013 | Moll et al. |
| 8,684,952 B2 | 4/2014 | Weitzner et al. |
| 8,736,212 B2 | 5/2014 | Sandhu et al. |
| 8,801,661 B2 | 8/2014 | Moll et al. |
| 9,283,046 B2 | 3/2016 | Walker et al. |
| 9,326,822 B2 | 5/2016 | Lewis et al. |
| 9,408,669 B2 | 8/2016 | Kokish et al. |
| 9,782,564 B2 | 10/2017 | Zirps et al. |
| 9,814,864 B2 | 11/2017 | Scarpine et al. |
| 9,825,455 B2 | 11/2017 | Sandhu et al. |
| 10,213,264 B2 | 2/2019 | Tanner et al. |
| 10,272,569 B2 | 4/2019 | Swarup et al. |
| 10,307,214 B2 | 6/2019 | Lathrop et al. |
| 10,357,330 B2 | 7/2019 | Fukushima et al. |
| 10,398,528 B2 | 9/2019 | Tao et al. |
| 10,449,007 B2 | 10/2019 | Deboeuf et al. |
| 10,449,008 B2 | 10/2019 | Miller et al. |
| 10,766,138 B2 | 9/2020 | Perplies et al. |
| 10,823,944 B2 | 11/2020 | Tamura et al. |
| 10,898,293 B2 | 1/2021 | Fukushima et al. |
| 10,919,161 B2 | 2/2021 | Smith et al. |
| 2002/0177789 A1 | 11/2002 | Ferry et al. |
| 2004/0254566 A1 | 12/2004 | Plicchi et al. |
| 2005/0075536 A1 | 4/2005 | Ostuka et al. |
| 2007/0060879 A1 | 3/2007 | Weitzner et al. |
| 2008/0243064 A1 | 10/2008 | Stahler et al. |
| 2009/0082722 A1 | 3/2009 | Munger et al. |
| 2012/0071752 A1 | 3/2012 | Sewell et al. |
| 2013/0279663 A1 | 10/2013 | Barker et al. |
| 2014/0276389 A1 | 9/2014 | Walker |
| 2015/0142013 A1 | 5/2015 | Tanner et al. |
| 2017/0007343 A1 | 1/2017 | Yu |
| 2017/0348060 A1 | 12/2017 | Blacker |
| 2018/0014906 A1 | 1/2018 | Fukushima et al. |
| 2018/0298970 A1 * | 10/2018 | Daugirdas ............ A61B 6/4476 |
| 2019/0128347 A1 * | 5/2019 | Leimbach .............. A61B 34/71 |
| 2019/0175887 A1 | 6/2019 | Shameli |
| 2019/0176320 A1 | 6/2019 | Smith et al. |
| 2020/0030056 A1 | 1/2020 | Bellows et al. |
| 2020/0030058 A1 | 1/2020 | Bellows et al. |
| 2021/0015566 A1 | 1/2021 | Lambrecht et al. |
| 2022/0381398 A1* | 12/2022 | Jones ..................... A61B 90/50 |

FOREIGN PATENT DOCUMENTS

| | | | | |
|---|---|---|---|---|
| EP | 2124800 | | 12/2009 | |
| GB | 2113650 A | * | 8/1983 | ......... B25J 19/0004 |
| JP | S6125787 A | * | 2/1986 | |
| JP | 2019098520 A | * | 6/2019 | ........... B25J 13/025 |
| WO | 2021011518 | | 1/2021 | |
| WO | 2021011533 | | 1/2021 | |
| WO | 2021011551 | | 1/2021 | |
| WO | 2021011554 | | 1/2021 | |
| WO | 2021094673 | | 5/2021 | |
| WO | 2022154975 | | 7/2022 | |
| WO | 2022154976 | | 7/2022 | |
| WO | 2022154977 | | 7/2022 | |
| WO | 2022154978 | | 7/2022 | |
| WO | 2022154980 | | 7/2022 | |

* cited by examiner

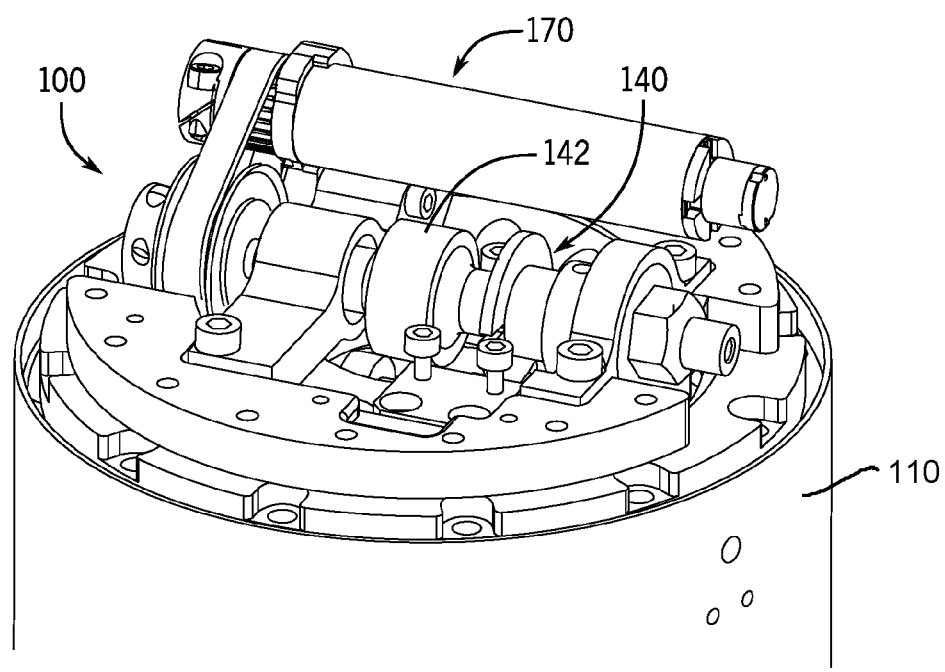
FIG. 7
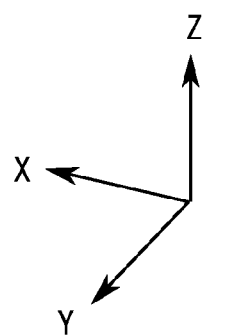

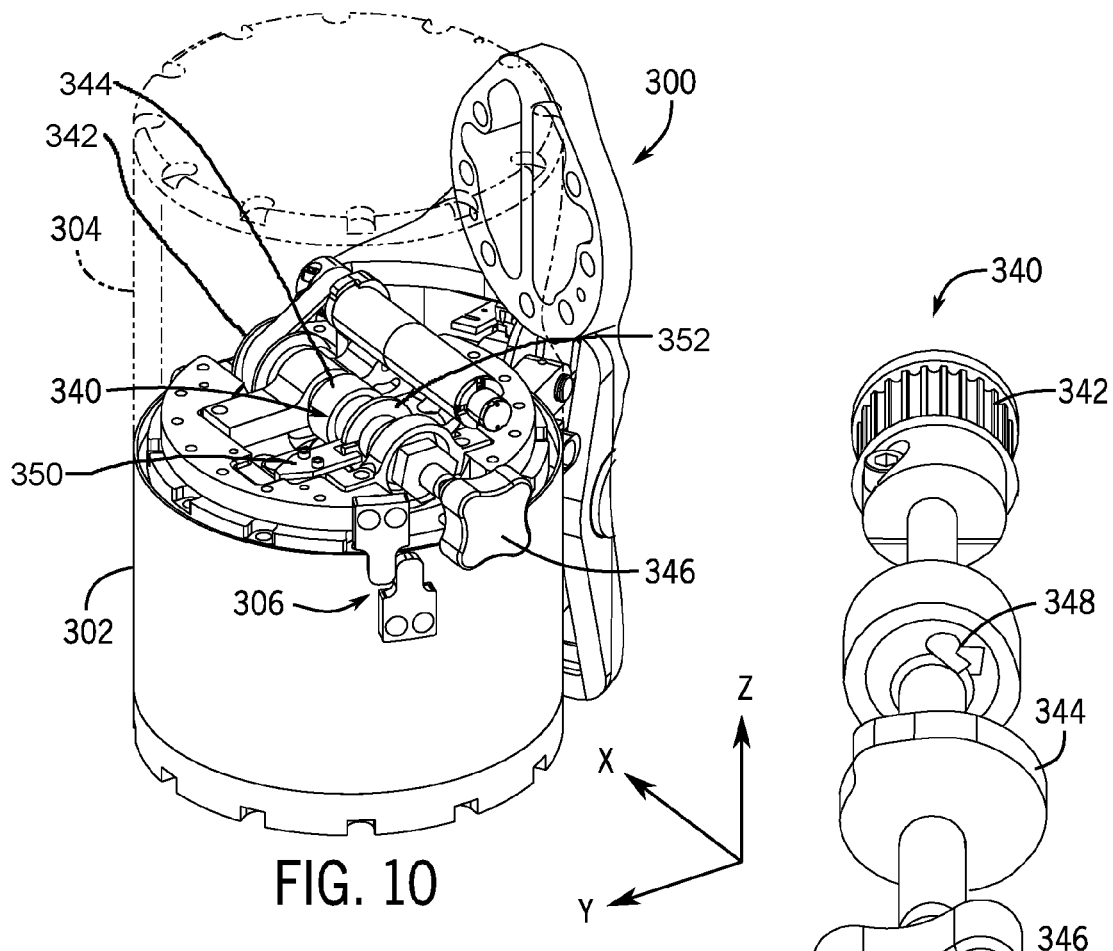
FIG. 10
FIG. 11
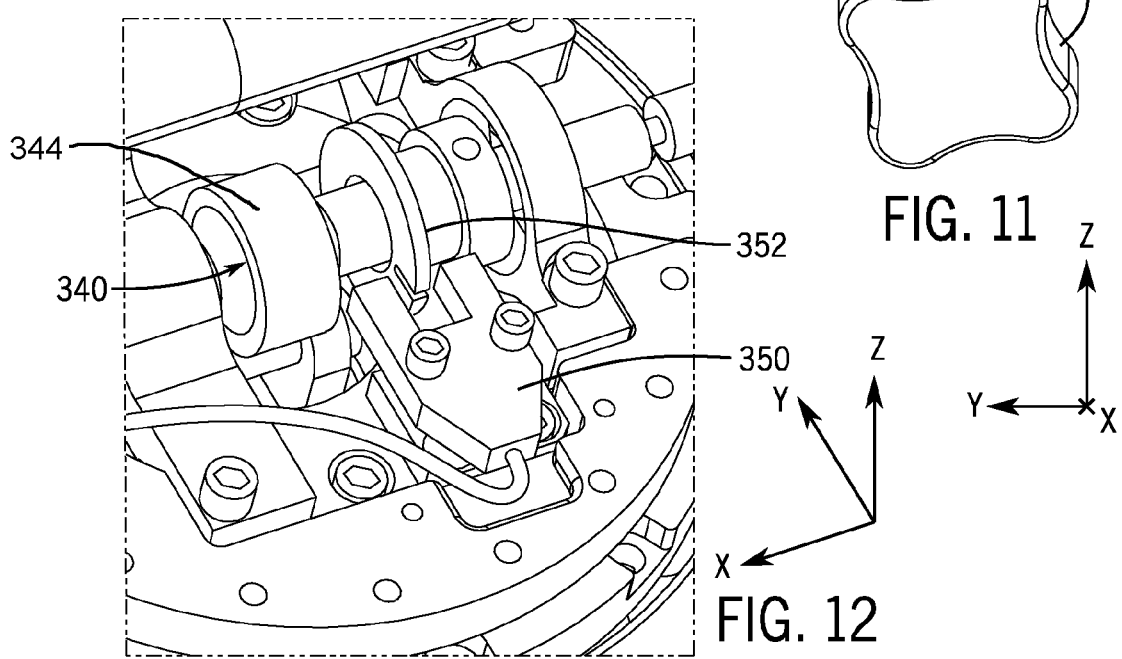
FIG. 12

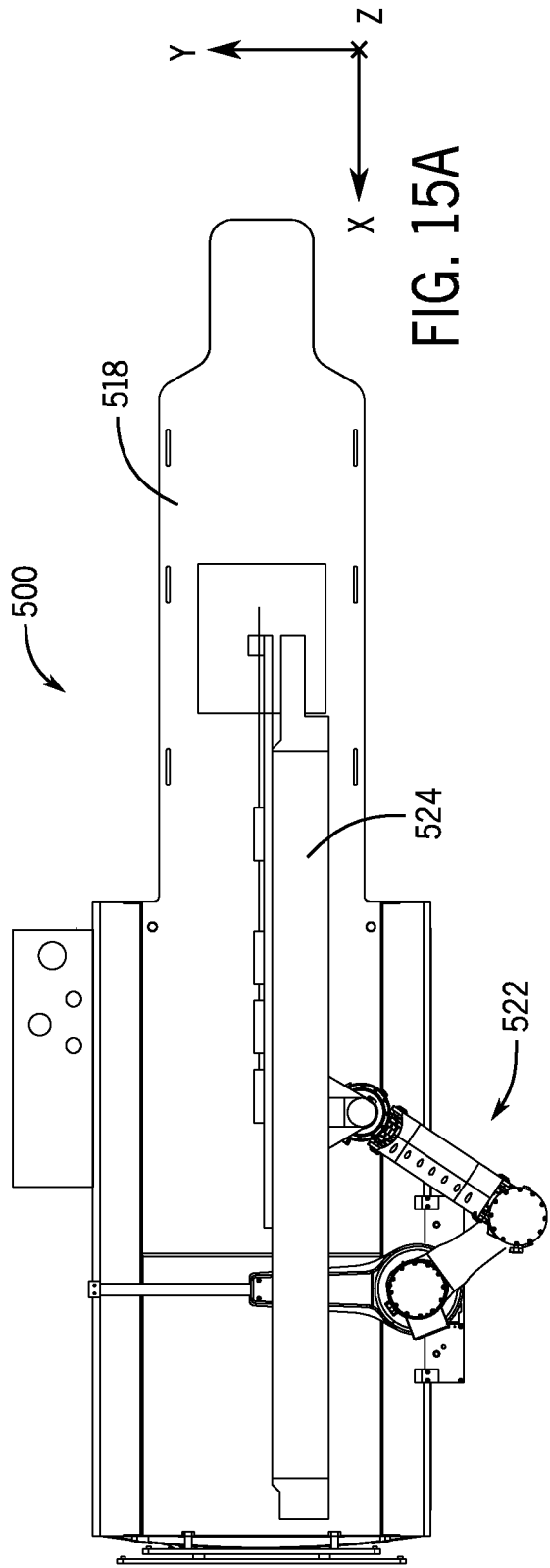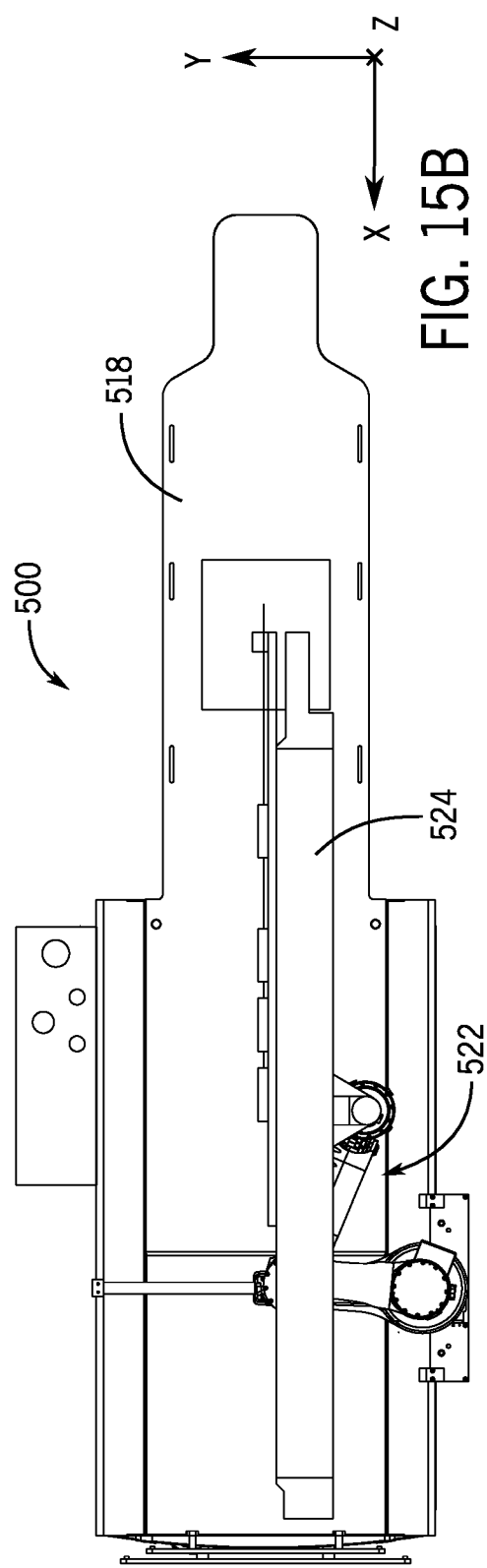

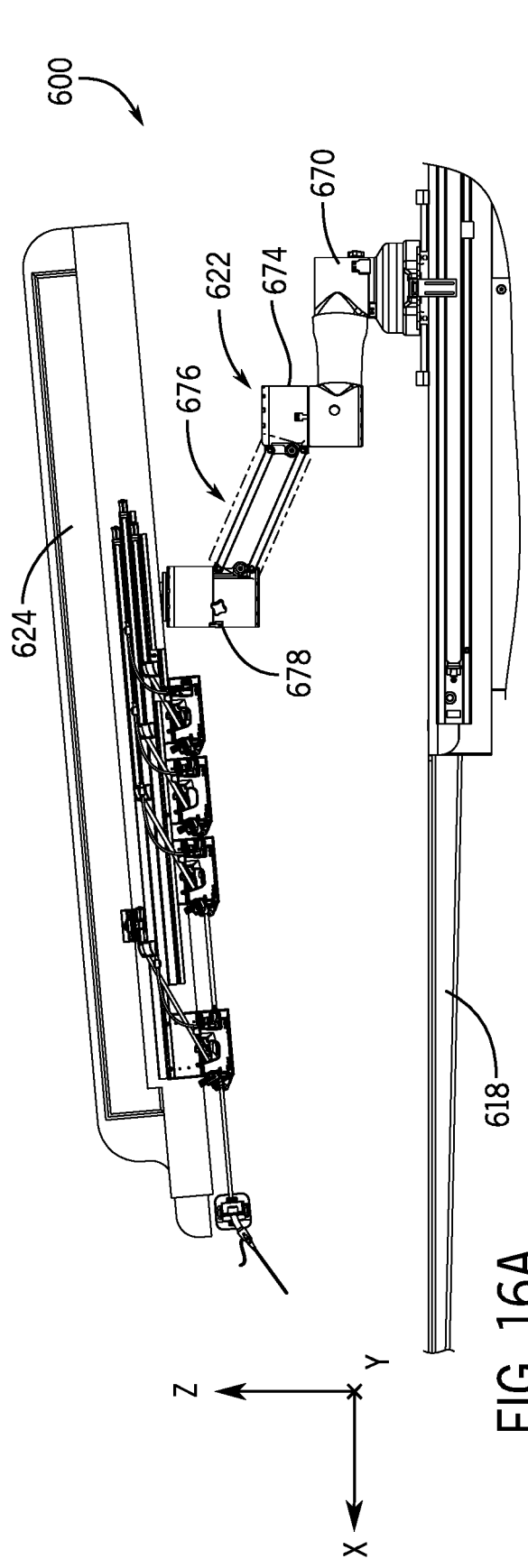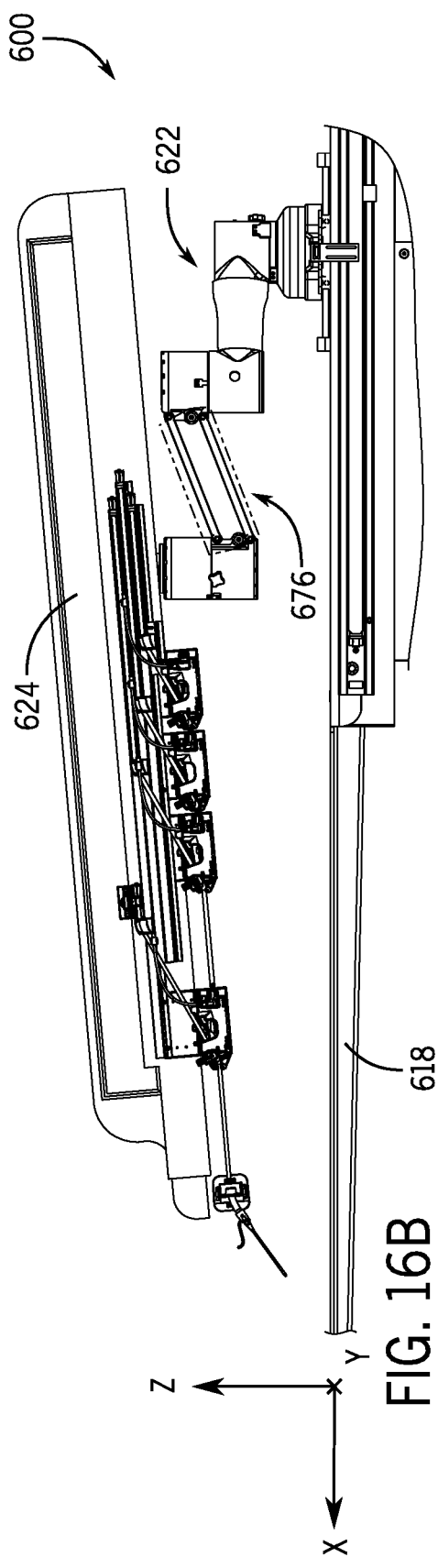

ROTATIONAL JOINT ASSEMBLY FOR ROBOTIC MEDICAL SYSTEM

FIELD

The present invention relates generally to the field of robotic medical procedure systems and, in particular, to rotational joints for such system.

BACKGROUND

Catheters and other elongated medical devices (EMDs) may be used for minimally-invasive medical procedures for the diagnosis and treatment of diseases of various vascular systems, including neurovascular intervention (NVI) also known as neurointerventional surgery, percutaneous coronary intervention (PCI) and peripheral vascular intervention (PVI). These procedures typically involve navigating a guidewire through the vasculature, and via the guidewire advancing a catheter to deliver therapy. The catheterization procedure starts by gaining access into the appropriate vessel, such as an artery or vein, with an introducer sheath using standard percutaneous techniques. Through the introducer sheath, a sheath or guide catheter is then advanced over a diagnostic guidewire to a primary location such as an internal carotid artery for NVI, a coronary ostium for PCI, or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example, a lesion. Contrast-enhanced images are also obtained while the physician delivers the guidewire or catheter so that the physician can verify that the device is moving along the correct path to the target location. While observing the anatomy using fluoroscopy, the physician manipulates the proximal end of the guidewire or catheter to direct the distal tip into the appropriate vessels toward the lesion or target anatomical location and avoid advancing into side branches.

Robotic catheter-based procedure systems have been developed that may be used to aid a physician in performing catheterization procedures such as, for example, NVI, PCI and PVI. Examples of NVI procedures include coil embolization of aneurysms, liquid embolization of arteriovenous malformations and mechanical thrombectomy of large vessel occlusions in the setting of acute ischemic stroke. In an NVI procedure, the physician uses a robotic system to gain target lesion access by controlling the manipulation of a neurovascular guidewire and microcatheter to deliver the therapy to restore normal blood flow. Target access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several embolization coils are deployed into the aneurysm through the microcatheter and used to block blood flow into the aneurysm. For treating arteriovenous malformations, a liquid embolic is injected into the malformation via a microcatheter. Mechanical thrombectomy to treat vessel occlusions can be achieved either through aspiration and/or use of a stent retriever. Depending on the location of the clot, aspiration is either done through an aspiration catheter, or through a microcatheter for smaller arteries. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter (or intermediate catheter) into the guide catheter.

In PCI, the physician uses a robotic system to gain lesion access by manipulating a coronary guidewire to deliver the therapy and restore normal blood flow. The access is enabled by seating a guide catheter in a coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or fractional flow reserve (FFR) measurements.

In PVI, the physician uses a robotic system to deliver the therapy and restore blood flow with techniques similar to NVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

When support at the distal end of a catheter or guidewire is needed, for example, to navigate tortuous or calcified vasculature, to reach distal anatomical locations, or to cross hard lesions, an over-the-wire (OTW) catheter or coaxial system is used. An OTW catheter has a lumen for the guidewire that extends the full length of the catheter. This provides a relatively stable system because the guidewire is supported along the whole length. This system, however, has some disadvantages, including higher friction, and longer overall length compared to rapid-exchange catheters (see below). Typically to remove or exchange an OTW catheter while maintaining the position of the indwelling guidewire, the exposed length (outside of the patient) of guidewire must be longer than the OTW catheter. A 300 cm long guidewire is typically sufficient for this purpose and is often referred to as an exchange length guidewire. Due to the length of the guidewire, two operators are needed to remove or exchange an OTW catheter. This becomes even more challenging if a triple coaxial, known in the art as a tri-axial system, is used (quadruple coaxial catheters have also been known to be used). However, due to its stability, an OTW system is often used in NVI and PVI procedures. On the other hand, PCI procedures often use rapid exchange (or monorail) catheters. The guidewire lumen in a rapid exchange catheter runs only through a distal section of the catheter, called the monorail or rapid exchange (RX) section. With a RX system, the operator manipulates the interventional devices parallel to each other (as opposed to with an OTW system, in which the devices are manipulated in a serial configuration), and the exposed length of guidewire only needs to be slightly longer than the RX section of the catheter. A rapid exchange length guidewire is typically 180-200 cm long. Given the shorter length guidewire and monorail, RX catheters can be exchanged by a single operator. However, RX catheters are often inadequate when more distal support is needed.

SUMMARY

In accordance with an embodiment, a rotational joint assembly for robotic medical system includes at least one arm segment and a rotational joint provided at one end of the arm segment. The rotational joint allows the arm segment to rotate about a rotational axis. The rotational joint includes a brake to lock rotation of the arm segment at the rotational joint and an actuator to selectively engage or disengage the brake. The actuator includes a cam having two stable regions separated by two transition regions, the two stable regions including a first stable region corresponding to engagement of the brake and a second stable region corresponding to disengagement of the brake.

BRIEF DESCRIPTION OF THE DRAWINGS

The invention will become more fully understood from the following detailed description, taken in conjunction with the accompanying drawings, wherein the reference numerals refer to like parts in which:

FIG. 7 is a perspective view of a portion of the example rotational joint of FIG. 5;

FIG. 10 is a perspective view of an example rotational joint with an example manual actuator;

FIG. 11 is a perspective view of an example camshaft with the manual actuator of FIG. 10;

FIG. 12 is a perspective view of a portion of the example rotational joint illustrating a sensor system;

FIGS. 15A and 15B are top views of the example catheter-based procedure system of FIG. 1 with the positioning system in different configurations;

FIGS. 16A and 16B illustrate operation of a system 600 with example 4-bar linkage;

DETAILED DESCRIPTION

Figure 1:
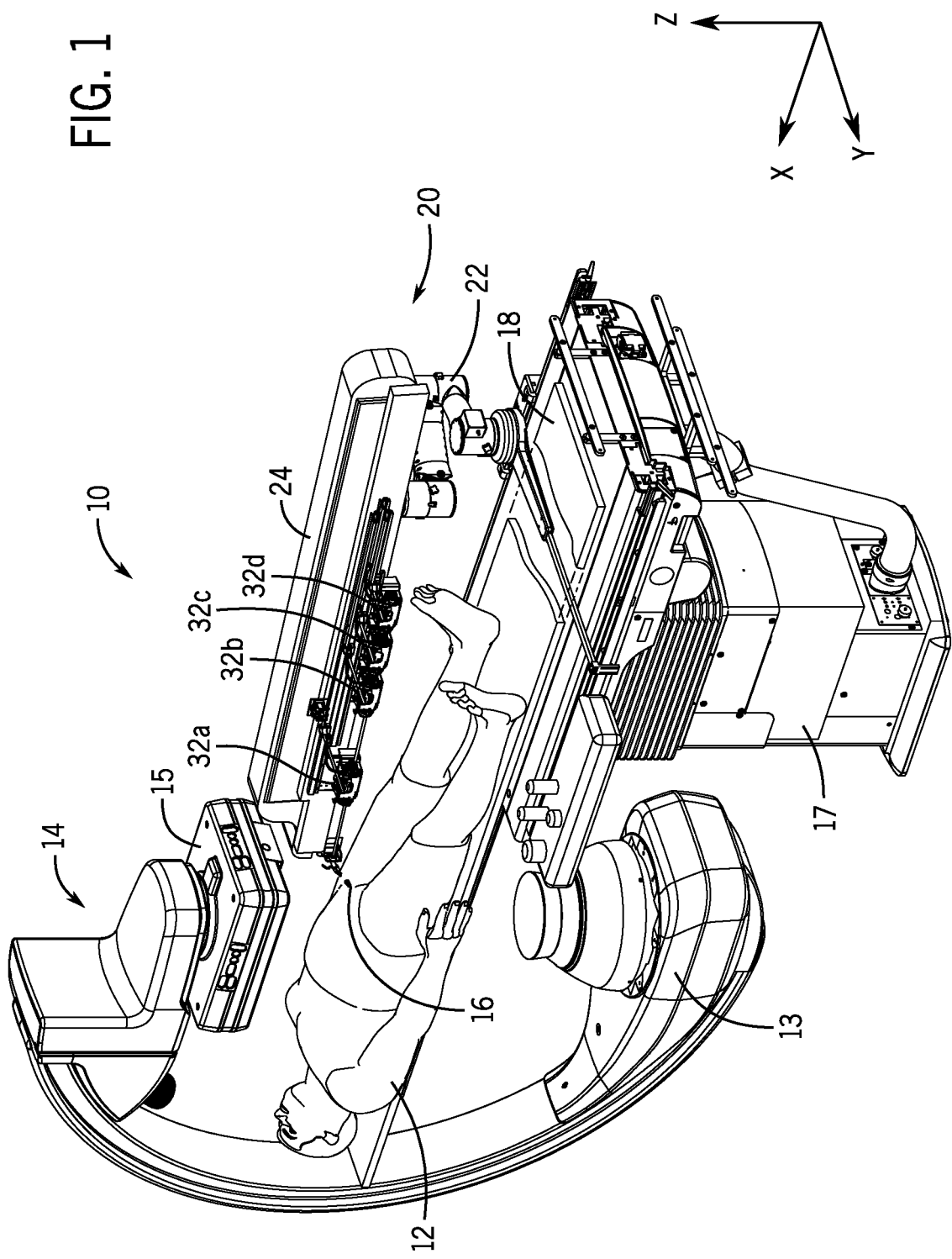
FIG. 1 is a perspective view of an example catheter-based procedure system in accordance with an embodiment.

FIG. 1 is a perspective view of an example catheter-based procedure system 10 in accordance with an embodiment. Catheter-based procedure system 10 may be used to perform catheter-based medical procedures, e.g., percutaneous intervention procedures such as a percutaneous coronary intervention (PCI) (e.g., to treat STEMI), a neurovascular interventional procedure (NVI) (e.g., to treat an emergent large vessel occlusion (ELVO)), peripheral vascular intervention procedures (PVI) (e.g., for critical limb ischemia (CLI), etc.). Catheter-based medical procedures may include diagnostic catheterization procedures during which one or more catheters or other elongated medical devices (EMDs) are used to aid in the diagnosis of a patient's disease. For example, during one embodiment of a catheter-based diagnostic procedure, a contrast media is injected onto one or more arteries through a catheter and an image of the patient's vasculature is taken. Catheter-based medical procedures may also include catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease. Therapeutic procedures may be enhanced by the inclusion of adjunct devices 54 (shown in FIG. 2) such as, for example, intravascular ultrasound (IVUS), optical coherence tomography (OCT), fractional flow reserve (FFR), etc. It should be noted, however, that one skilled in the art would recognize that certain specific percutaneous intervention devices or components (e.g., type of guidewire, type of catheter, etc.) may be selected based on the type of procedure that is to be performed. Catheter-based procedure system 10 can perform any number of catheter-based medical procedures with minor adjustments to accommodate the specific percutaneous intervention devices to be used in the procedure.

Catheter-based procedure system 10 includes, among other elements, a bedside unit 20 and a control station (not shown). Bedside unit 20 includes a robotic drive 24 and a positioning system 22 that are located adjacent to a patient 12. Patient 12 is supported on a patient table 18. The positioning system 22 is used to position and support the robotic drive 24. The positioning system 22 may be, for example, a robotic arm, an articulated arm, a holder, etc. The positioning system 22 may be attached at one end to, for example, the patient table 18 (as shown in FIG. 1), a base, or a cart. The other end of the positioning system 22 is attached to the robotic drive 24. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In an embodiment, patient table 18 is operably supported by a pedestal 17, which is secured to the floor and/or earth. Patient table 18 is able to move with multiple degrees of freedom, for example, roll, pitch, and yaw, relative to the pedestal 17. Bedside unit 20 may also include controls and displays 46 (shown in FIG. 2). For example, controls and displays may be located on a housing of the robotic drive 24.

Generally, the robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow a user or operator to perform a catheter-based medical procedure via a robotic system by operating various controls such as the controls and inputs located at the control station. Bedside unit 20, and in particular robotic drive 24, may include any number and/or combination of components to provide bedside unit 20 with the functionality described herein. The robotic drive 24 includes a plurality of device modules 32a-d mounted to a rail or linear member. Each of the device modules 32a-d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with the control station (not shown), allowing signals generated by the user inputs of the control station to be transmitted wirelessly or via hardwire to the bedside unit 20 to control various functions of bedside unit 20. As discussed below, control station 26 may include a control computing system 34 (shown in FIG. 2) or be coupled to the bedside unit 20 through the control computing system 34. Bedside unit 20 may also provide feedback signals (e.g., loads, speeds, operating conditions, warning signals, error codes, etc.) to the control station, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components. The control station or other similar control system may be located either at a local site (e.g., local control station 38 shown in FIG. 2) or at a remote site (e.g., remote control station and computer system 42 shown in FIG. 2). Catheter procedure system 10 may be operated by a control station at the local site, a control station at a remote site, or both the local control station and the remote control station at the same time. At a local site, a user or operator and the control station are located in the same room or an adjacent room to the patient 12 and bedside unit 20. As used herein, a local site is the location of the bedside unit 20 and a patient 12 or subject (e.g., animal or cadaver) and the remote site is the location of a user or operator and a control station used to control the bedside unit 20 remotely. A control station (and a control computing system) at a remote site and the bedside unit 20 and/or a control computing system at a local site may be in communication using communication systems and services 36 (shown in FIG. 2), for example, through the Internet. In an embodiment, the remote site and the local (patient) site are away from one another, for example, in different rooms in the same building, different buildings in the same city, different cities, or other different locations where the remote site does not have physical access to the bedside unit 20 and/or patient 12 at the local site.

The control station generally includes one or more input modules 28 configured to receive user inputs to operate various components or systems of catheter-based procedure system 10. In the embodiment shown, control station allows the user or operator to control bedside unit 20 to perform a catheter-based medical procedure. For example, input modules 28 may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In one embodiment, input modules 28 may include one or more touch screens, joysticks, scroll wheels, and/or buttons. In addition to input modules 28, the control station 26 may use additional user controls 44 (shown in FIG. 2) such as foot switches and microphones for voice commands, etc. Input modules 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. When an emergency stop button is pushed, the power (e.g., electrical power) is shut off or removed to bedside unit 20. When in a speed control mode, a multiplier button acts to increase or decrease the speed at which the associated component is moved in response to a manipulation of input modules 28. When in a position control mode, a multiplier button changes the mapping between input distance and the output commanded distance. Device selection buttons allow the user or operator to select which of the percutaneous intervention devices loaded into the robotic drive 24 are controlled by input modules 28. Automated move buttons are used to enable algorithmic movements that the catheter-based procedure system 10 may perform on a percutaneous intervention device without direct command from the user or operator 11. In one embodiment, input modules 28 may include one or more controls or icons (not shown) displayed on a touch screen (that may or may not be part of a display), that, when activated, causes operation of a component of the catheter-based procedure system 10. Input modules 28 may also include a balloon or stent control that is configured to inflate or deflate a balloon and/or deploy a stent. Each of the input modules 28 may include one or more buttons, scroll wheels, joysticks, touch screen, etc. that may be used to control the particular component or components to which the control is dedicated. In addition, one or more touch screens may display one or more icons (not shown) related to various portions of input modules 28 or to various components of catheter-based procedure system 10.

Catheter-based procedure system 10 also includes an imaging system 14. Imaging system 14 may be any medical imaging system that may be used in conjunction with a catheter based medical procedure (e.g., non-digital X-ray, digital X-ray, CT, MRI, ultrasound, etc.). In an exemplary embodiment, imaging system 14 is a digital X-ray imaging device that is in communication with the control station. In one embodiment, imaging system 14 may include a C-arm (shown in FIG. 1) that allows imaging system 14 to partially or completely rotate around patient 12 in order to obtain images at different angular positions relative to patient 12 (e.g., sagittal views, caudal views, anterior-posterior views, etc.). In one embodiment imaging system 14 is a fluoroscopy system including a C-arm having an X-ray source 13 and a detector 15, also known as an image intensifier.

Imaging system 14 may be configured to take X-ray images of the appropriate area of patient 12 during a procedure. For example, imaging system 14 may be configured to take one or more X-ray images of the head to diagnose a neurovascular condition. Imaging system 14 may also be configured to take one or more X-ray images (e.g., real time images) during a catheter-based medical procedure to assist the user or operator 11 of control station 26 to properly position a guidewire, guide catheter, microcatheter, stent retriever, coil, stent, balloon, etc. during the procedure. The image or images may be displayed on display 30. For example, images may be displayed on a display to allow the user or operator to accurately move a guide catheter or guidewire into the proper position.

In order to clarify directions, a rectangular coordinate system is introduced with X, Y, and Z axes. The positive X axis is oriented in a longitudinal (axial) distal direction, that is, in the direction from the proximal end to the distal end, stated another way from the proximal to distal direction. The Y and Z axes are in a transverse plane to the X axis, with the positive Z axis oriented up, that is, in the direction opposite of gravity, and the Y axis is automatically determined by right-hand rule.

Figure 2:
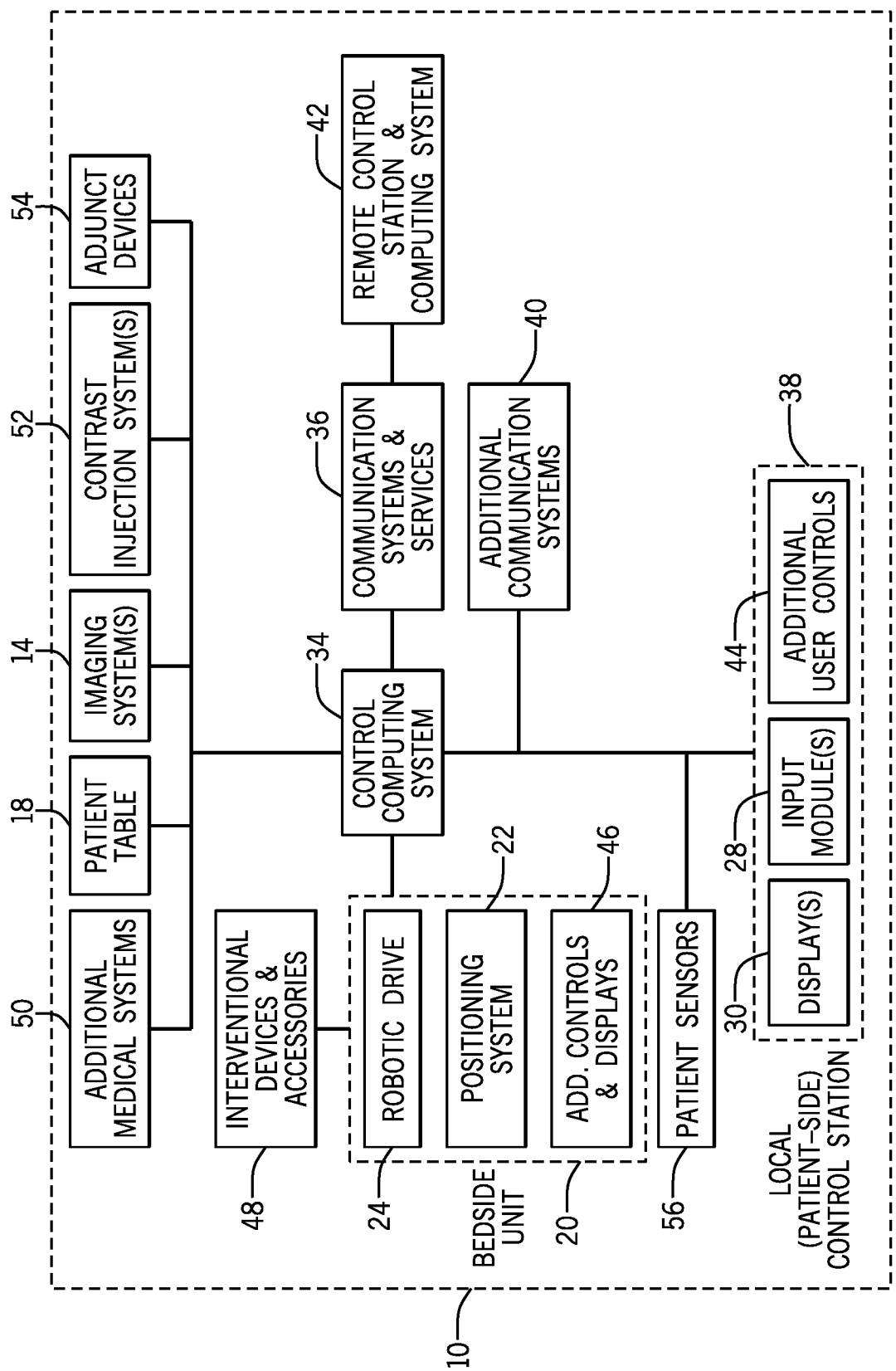
FIG. 2 is a schematic block diagram of an exemplary catheter-based procedure system in accordance with an embodiment.

FIG. 2 is a block diagram of catheter-based procedure system 10 in accordance with an example embodiment. Catheter-procedure system 10 may include a control computing system 34. Control computing system 34 may physically be, for example, part of a control station. Control computing system 34 may generally be an electronic control unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, communications systems and services 36 (e.g., Internet, firewalls, cloud services, session managers, a hospital network, etc.), a local control station 38, additional communications systems 40 (e.g., a telepresence system), a remote control station and computing system 42, and patient sensors 56 (e.g., electrocardiogram (ECG) devices, electroencephalogram (EEG) devices, blood pressure monitors, temperature monitors, heart rate monitors, respiratory monitors, etc.). The control computing system is also in communication with imaging system 14, patient table 18, additional medical systems 50, contrast injection systems 52 and adjunct devices 54 (e.g., IVUS, OCT, FFR, etc.). The bedside unit 20 includes a robotic drive 24, a positioning system 22 and may include additional controls and displays 46. As mentioned above, the additional controls and displays may be located on a housing of the robotic drive 24. Interventional devices and accessories 48 (e.g., guidewires, catheters, etc.) interface to the bedside system 20. In an embodiment, interventional devices and accessories 48 may include specialized devices (e.g., IVUS catheter, OCT catheter, FFR wire, diagnostic catheter for contrast, etc.) which interface to their respective adjunct devices 54, namely, an IVUS system, an OCT system, and FFR system, etc.

In various embodiments, control computing system 34 is configured to generate control signals based on the user's interaction with input modules 28 (e.g., of a control station such as a local control station 38 or a remote control station 42) and/or based on information accessible to control computing system 34 such that a medical procedure may be performed using catheter-based procedure system 10. The local control station 38 includes one or more displays 30, one or more input modules 28, and additional user controls 44. The remote control station and computing system 42 may include similar components to the local control station 38. The remote 42 and local 38 control stations can be different and tailored based on their required functionalities. The additional user controls 44 may include, for example, one or more foot input controls. The foot input control may be configured to allow the user to select functions of the imaging system 14 such as turning on and off the X-ray and scrolling through different stored images. In another embodiment, a foot input device may be configured to allow the user to select which devices are mapped to scroll wheels included in input modules 28. Additional communication systems 40 (e.g., audio conference, video conference, telepresence, etc.) may be employed to help the operator interact with the patient, medical staff (e.g., angio-suite staff), and/or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

As mentioned, control computing system 34 is in communication with bedside unit 20 which includes a robotic drive 24, a positioning system 22 and may include additional controls and displays 46, and may provide control signals to the bedside unit 20 to control the operation of the motors and drive mechanisms used to drive the percutaneous intervention devices (e.g., guidewire, catheter, etc.). The various drive mechanisms may be provided as part of a robotic drive 24.

Figure 3:
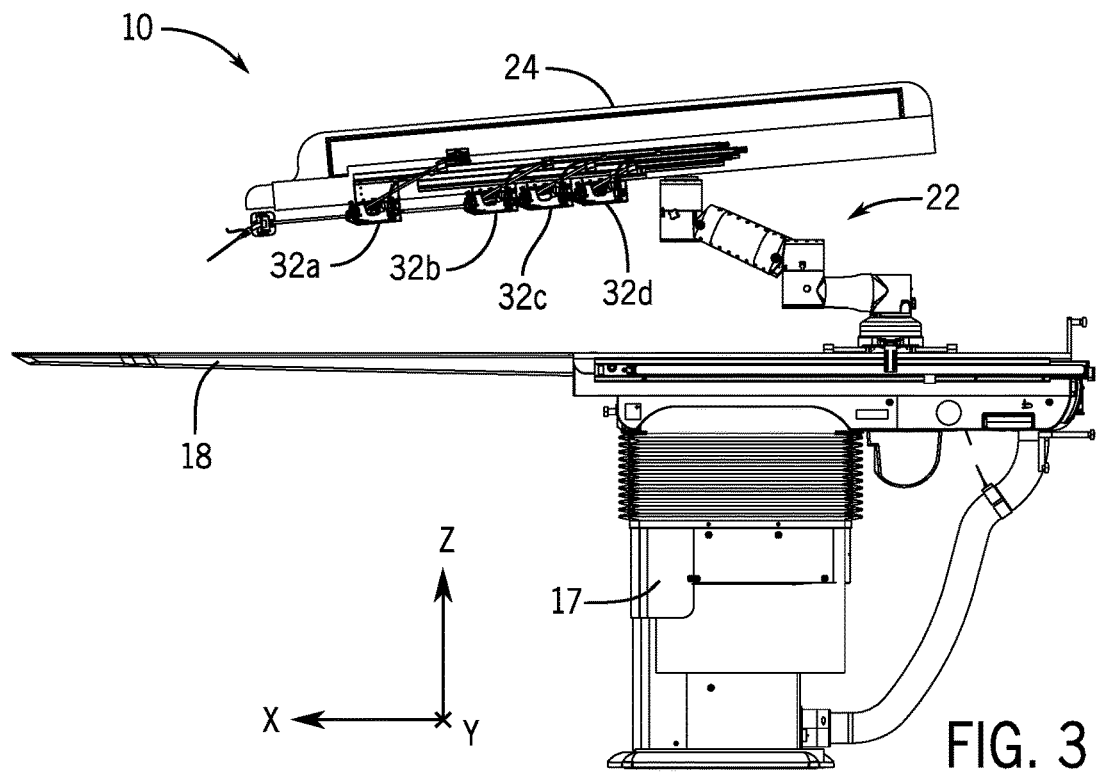
FIG. 3 is a side view of example catheter-based procedure system of FIG. 1 with certain components removed for clarity.

Referring now to FIG. 3, a side view of the example catheter-based procedure system 10 of FIG. 1 is illustrated with certain components (e.g., patient, C-arm) removed for clarity. As described above with reference to FIG. 1, the patient table 18 is supported on the pedestal 17, and the robotic drive 24 is mounted to the patient table with a positioning system 22. The positioning system 22 allows manipulation of the robotic drive 24 relative to the patient table 18. In this regard, the positioning system 22 is securely mounted to the patient table 18 and includes various joints and links/arm segments to allow the manipulation, as described below with reference to FIG. 4.

Figure 4:
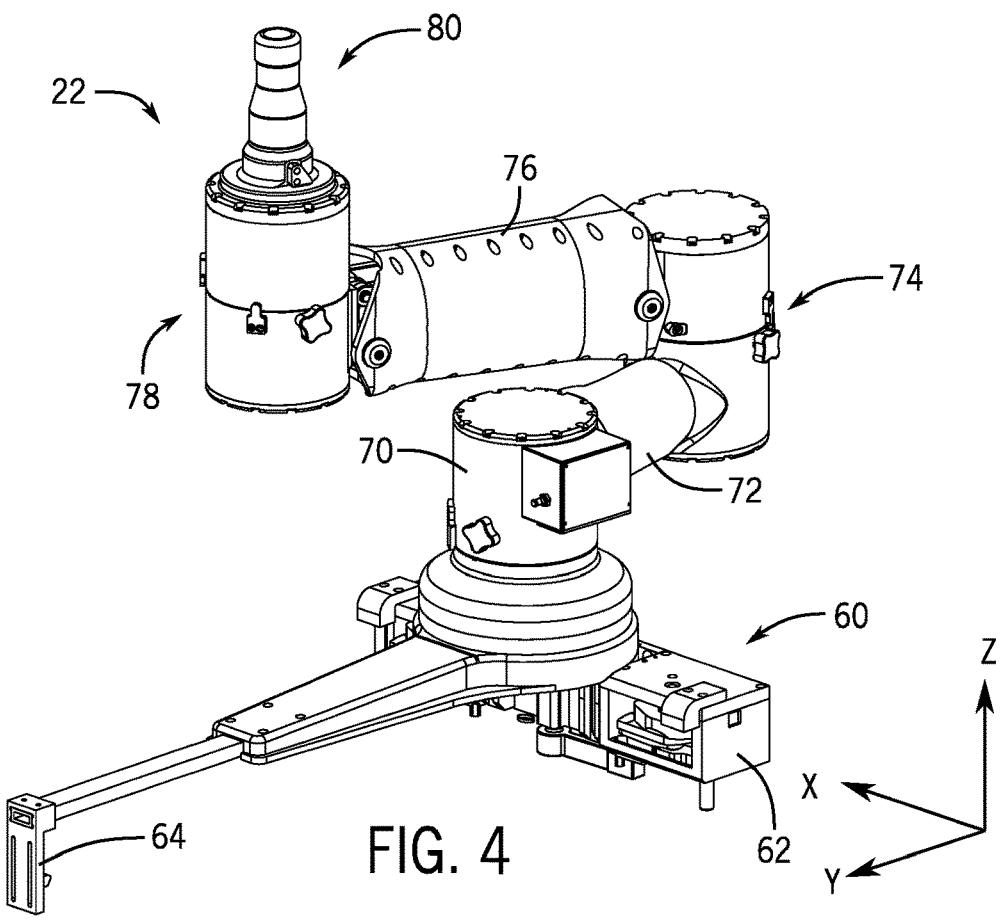
FIG. 4 is a perspective view of an example positioning system for a robotic drive in accordance with an embodiment.

FIG. 4 is a perspective view of an example positioning system 22 for a robotic drive in accordance with an embodiment. The positioning system 22 includes a mounting arrangement 60 to securely mount the positioning system 22 to the patient table 18. The mounting arrangement 60 includes an engagement mechanism to engage a first engagement member with a first longitudinal rail and a second engagement member with a second longitudinal rail of the patient table 18 to removably secure the positioning system to the patient table 18.

The positioning system 22 includes various segments and joints coupling to allow the robotic drive 24 to be positioned as desired, for example, relative to the patient. The positioning system 22 includes a first rotational joint 70 coupled to the mounting arrangement 60. The first rotational joint 70 allows rotation of a first arm segment 72, or link, about a rotational axis. In the illustrated example, the mounting arrangement 60 is in a substantially horizontal plane (e.g., the plane of the patient table 18), and the rotational axis is substantially vertical and runs through the center of the first rotational joint 70. The first rotational joint 70 can include circuitry to allow a user to control various operations related to the first rotational joint 70, such as locking or releasing the rotational movement.

In the illustrated example, the first arm segment 72 is substantially horizontal with a first end coupled to the first rotational joint 70. The second end of the first arm segment 72 is coupled to a second rotational joint 74. In addition, the second rotational joint 74 is also coupled to a first end of a second arm segment 76. Thus, the second rotational joint 74 allows rotation of the second arm segment 76 relative to the first arm segment 72. As with the first rotational joint 70, the second rotational joint 74 allows rotation about a substantially vertical axis running through the center of the second rotational joint 74.

In the illustrated example, a second end of the second arm segment 76 is coupled to a third rotational joint 78. The third rotational joint 78 includes a post 80 to allow mounting of the robotic drive 24 to the positioning system 22. Thus, the third rotational joint 78 allows rotation of the robotic drive 24 relative to the second arm segment 76. The third rotational joint 78 allows rotation about a substantially vertical axis running through the center of the third rotational joint 78.

In one example, the second arm segment 76 includes a 4-bar linkage which can allow limited vertical movement of third rotational joint 78 relative to the second rotational joint 74. In this regard, the 4-bar linkage can allow vertical movement of the third rotational join 78, while maintaining the substantially vertical orientation of the third rotational joint 78 and the post 80.

The example positioning system of FIG. 4 includes three rotary joints 70, 74, 78 and two arm segments 72, 76. This configuration provides for significant flexibility in positioning of the robotic drive. In particular the use of three rotary joints 70, 74, 78 provides flexibility in positioning of the robotic drive in two degrees of freedom. The three rotary joints 70, 74, 78 allow movement of the drive in a longitudinal direction (direction from head to toe of patient) above the patient table 18 and in a traverse direction (direction from left to right of patient) across the patient table 18. Thus, positioning in a large area relative to the patient is made available for use during a procedure. In addition, the arrangement allows orientation of the robotic drive at different angles relative to the longitudinal axis of the patient table (i.e., different yaw angles). Further, as noted above, as well as below with reference to FIGS. 16A and 16B, the use of the 4-bar linkage can provide an additional degree of freedom in the vertical direction.

Figure 5:
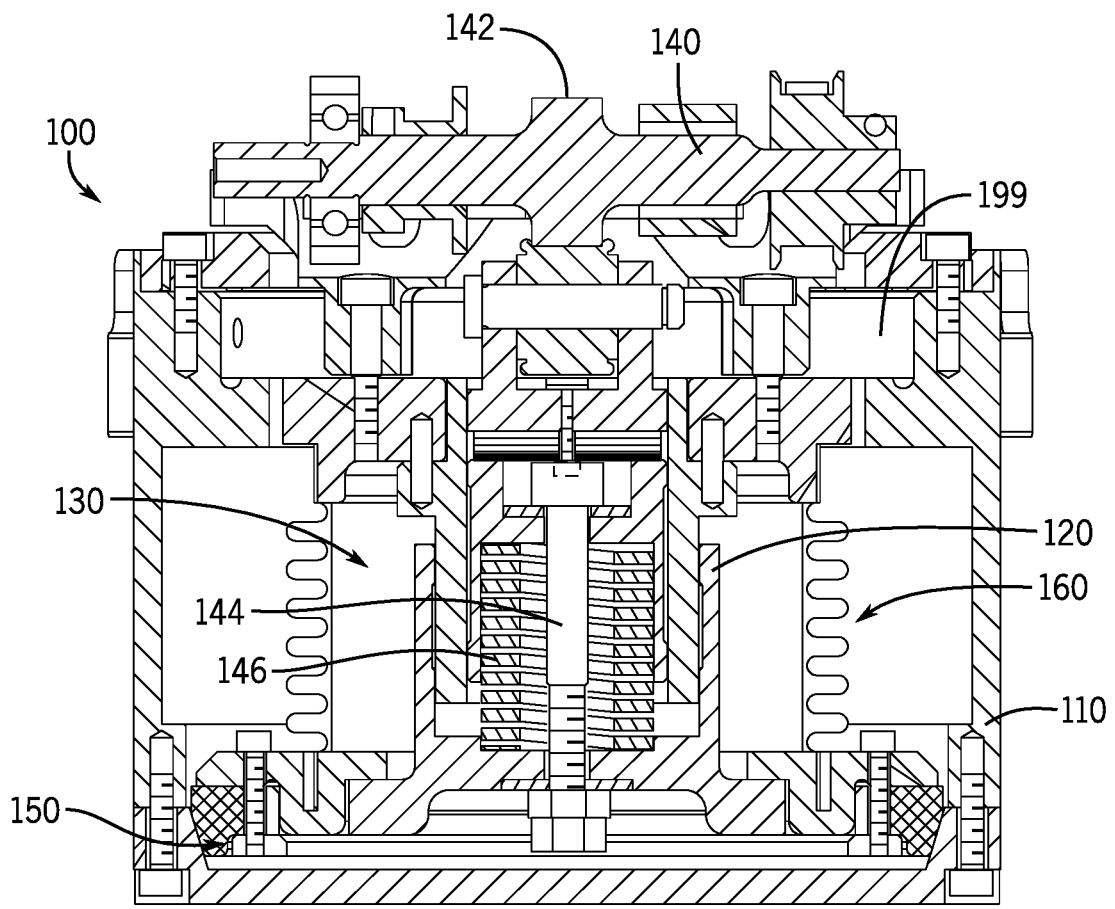
FIG. 5 is a cross-sectional view of an example rotational joint in accordance with an embodiment.

FIG. 5 is a cross-sectional view of an example rotational joint 100 in accordance with an embodiment. The example rotational joint 100 may be implemented in one or more of first rotational joint 70, second rotational joint 74 or the third rotational joint 78 of the positioning system 22 described above with reference to FIG. 4 above. The rotational joint 100 allows an outer housing 110 (and a component such as an arm segment coupled to the outer housing 110) to rotate relative to an inner housing 120 (and a component such as an arm segment coupled to the inner housing 120) about a rotational axis. The rotational axis can extend substantially vertically through the rotational joint 100. The rotational joint 100 further includes a brake system 130 to allow a user to selectively lock or unlock the rotational movement at the rotational joint 100.

In various examples described herein, the rotational joint 100 includes a brake system 130 which provides a sufficiently high locking or holding torque (e.g., 80 Nm) to ensure locking of the rotational joint 100. Further, the brake system 130 in accordance with the various examples described herein provide infinite resolution. For example, the rotational movement may be locked at any position of the inner housing 110 relative to the outer housing 120. In this regard, the brake system 130 is a gear-less system and does not rely on discrete points (e.g., gear teeth) for locking. Additionally, the lack of discrete points such as gear teeth in a geared brake system results in a brake system 130 with minimal or no backlash during braking or locking.

In the example rotational joint 100 of FIG. 1, the brake system 130 is actuated by a camshaft 140 having a cam 142. The camshaft 140 is driven by a motor to rotate the camshaft 140 and, along with it, the cam 140, as described in greater detail below with reference to FIG. 7. The cam 142 is shaped to rotate through a cycle during which the cam 142 causes engagement and disengagement of the brake 150. An example cam 142 is described below in greater detail with reference to FIG. 8.

A resilient component, such as a spring 146, is provided to pre-load or bias the brake bolt 144 upward. Pre-loading of the brake bolt 144 with the spring 146 allows for some over-travel, so desired clamping load on the friction surfaces can be achieved with some variation in the travel of the cam 142. Once travel of the cam 142 overcomes the preload from the spring 146, full force from the cam is applied to the brake 150, with slight increase in force with increased travel of the cam. With a relatively low spring constant, wearing of the system results in little change in the engagement force of the brake 150.

As the cam 142 rotates to a locked position, the downward force applied by the cam 142 on a follower results in the brake bolt 144 becoming unloaded, causing engagement of a brake 150, an example of which is described in greater detail below with reference to FIGS. 9A-9D. As noted above, the engagement of the brake 150 provides a sufficiently high locking or holding torque (e.g., 80 Nm) to ensure locking of the rotational joint 100. As the cam further rotates to the unlocked position, the downward force is removed, and the load from the spring 146 is returned to the brake bolt 144, causing disengagement of the brake 150.

Figure 6:
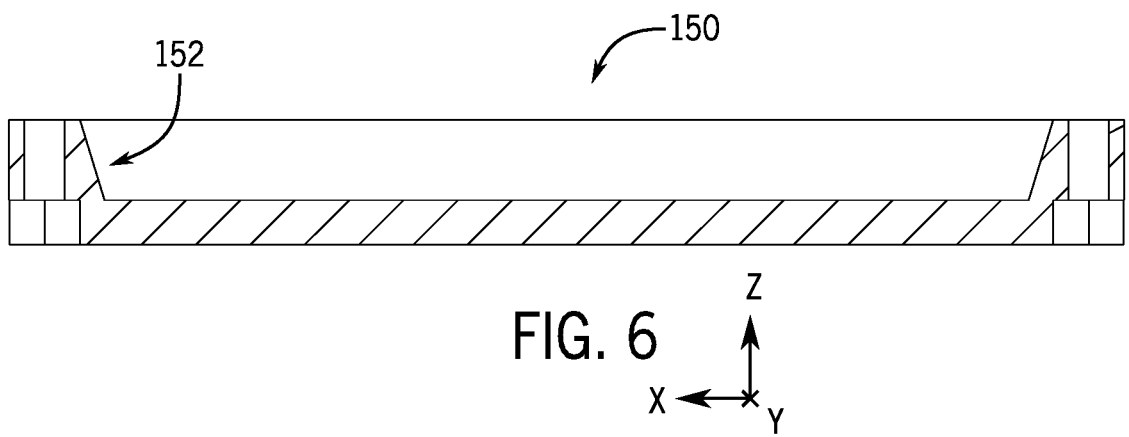
FIG. 6 is a cross-section side view of a portion of an example braking system for use with the rotational joint o FIG. 5.

In the example illustrated in FIG. 5, the brake 150 of the rotational joint 100 is provided with a first brake component that is coupled to the outer housing 110 and a second brake component coupled to the inner housing 120. When the brake is engaged, the first brake component and the second brake component engage each other, resulting in locking of the rotational joint 100. In the example illustrated in FIG. 5, the brake 150 includes a cup 152 coupled to the outer housing 110 and a cone 154 coupled to the inner housing 120. The cup 152 has a conical inner perimeter, as more clearly illustrated in FIG. 6, which provides a cross-sectional side view of the cup 152. The conical inner perimeter of the cup 152 coupled to the outer housing 110 corresponds to the cone 154 of the inner housing 120. Thus, during engagement of the brake 150, the cone 154 is received within the cup 152 and comes into contact with the inner perimeter of the cup 152. The inner perimeter of the cup 152 and the cone 154 form frictional surfaces which provide braking torque. The cup 152 and the cone 154 may be formed of any of a variety of materials. In one example, the cone 154 is formed of Victrex 450FC30 PEEK (a "10/10/10" PEEK), and the cup 152 is formed of a hard anodized aluminum. These materials provide high, repeatable friction and possess good wear properties.

The frictional surfaces of the cup 152 and the cone 154 provide continuous braking surfaces, thus providing infinite resolution for braking. Further, the continuous braking results in minimal or no backlash between the frictional surfaces of the brake 150.

In various examples, the inner perimeter of the cup 152 is conical with a cone angle selected to provide sufficiently high braking torque while avoiding self-locking. The cone angle is measured as the angle between the conical perimeter of the cup 152 and the vertical. If the cone angle is too small, self-locking becomes more likely, as the brake may not disengage when rotation of the cam the load from the spring 146 to be returned to the brake bolt 144. Accordingly, the cone angle should be sufficient to allow the cup to disengage upon removal of the downward force. In various examples, the conical inner perimeter of the cup 152 has a cone angle of between about 15 degrees and about 30 degrees. In one particular example, the conical inner perimeter of the cup 152 has a cone angle of about 17 degrees.

Referring now to FIG. 7, a perspective view of a portion of the example rotational joint 100 of FIG. 5 is illustrated. As described above with reference to FIG. 5, the rotational joint 100 includes a camshaft 140 having a cam 142 to selectively engage or disengage the brake 150. As illustrated in FIG. 7, the cam 142 is positioned on a camshaft driven by a motor 170. The motor 170 may be controlled by a user input for engagement or disengagement of the brake 150. The motor 170 drives the camshaft 140 through a belt drive coupling the motor 170 to the camshaft 140. Thus, based upon the user input, the motor 170 can drive the camshaft 140 to position the cam in a desired position. For example, the cam 142 can be positioned to cause engagement of the brake 150 or disengagement of the brake 150.

Figure 8:
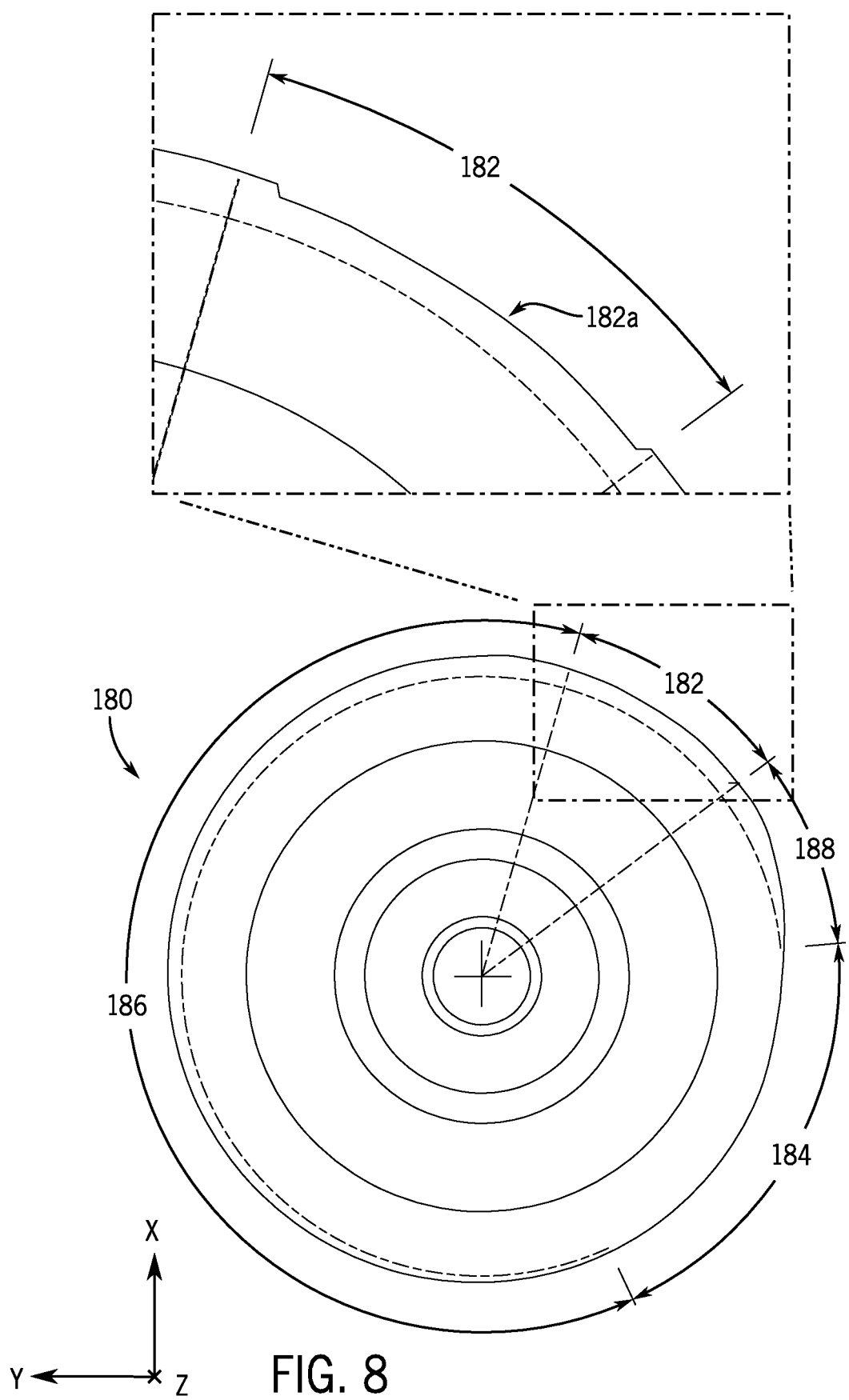
FIG. 8 is a side view of an example cam for use with the example rotational joint of FIG. 5.

Referring now to FIG. 8, a side view of an example cam 180 for use with the example rotational joint 100 of FIG. 5 is illustrated. The example cam 180 is a bi-stable cam with two stable regions separated by two transition regions. As illustrated in the example of FIG. 8, the cam 180 includes a stable locked (or engaged) region 182 at which the cam 180 generally has a greater radius than other regions of the cam 180. The greater radius causes the cam to apply a downward force on a follower to cause unloading of the brake bolt 144 described above with reference to FIG. 5.

The cam 180 includes a second stable region at the stable unlocked (or disengaged) region 184 at which the cam has a smaller radius than other regions of the cam 180. The smaller radius causes removal of the downward force on the follower causing the load from the spring 146 to be returned to the brake bolt 144.

The two stable regions 182, 184 are separated by two transition regions 186, 188. The first transition region 186 is a gradual transition region during which the cam rotates (counterclockwise in FIG. 8) from the stable unlocked region 184 to the stable locked region 182. The second transition region 188 is a rapid transition region during which the cam rotates from the stable locked region 182 to the stable unlocked region 184. Thus, the time required to unlock the brake (i.e., rotating the cam from the stable locked region 182 to the stable unlocked region 184 via the rapid transition region 188) is low since very little rotation of the camshaft is needed. On the other hand, the time required to lock the brake (i.e., rotating the cam from the stable unlocked region 184 to the stable locked region 182 via the gradual transition region 186) is significant since larger rotation of the camshaft is needed. In other examples, the positions of the gradual transition region 186 and the rapid transition region 188 may be switched, or the direction of rotation of the camshaft may be reversed.

The stable locked region 182 of the cam 80 illustrated in FIG. 8 provides a safety feature that prevents inadvertent disengagement of the brake. As illustrated in the inset of FIG. 8, a part of the stable locked region 182 is provided with a dwell region 182a, which has a lower radius than the outer edges of the stable locked region 182. The dwell region 182a provides a stable area which prevents unintended rotation of the cam out of the stable locked region 182. For example, if electrical power to the rotational joint 100 is lost while the brake is engaged, the brake will not become disengaged since at least some energy is required to move the cam out of the dwell region 182a of the stable locked region 182.

FIGS. 9A-9D illustrate an example operational cycle of an example braking system in accordance with an embodiment. The example braking system 200 includes a brake 210 with a cup 214 coupled to an outer housing 212 and a cone 216 coupled to an inner housing. The inner housing and the outer housing are rotatable relative to each other, and the braking system 200 selectively locks or unlocks the rotation. The braking system 200 is provided with a spring 218 which preloads a brake bolt, as described above with reference to FIGS. 5-8. A cam 220, similar to the cam 180 described above with reference to FIGS. 9A-9D, selectively causes engagement or disengagement of the brake 210.

Figure 9:
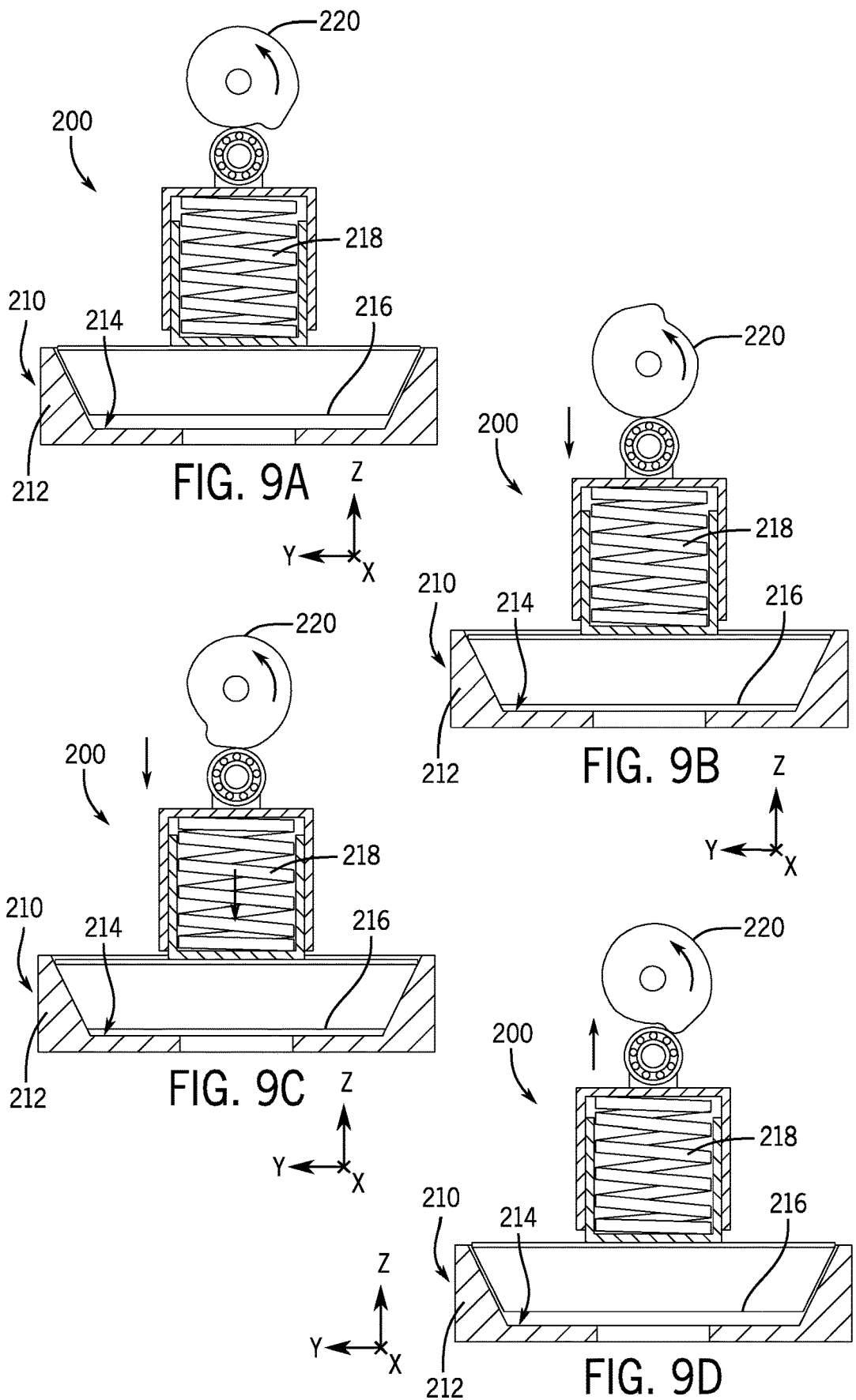
FIGS. 9A-9D illustrate an example operational cycle of an example braking system in accordance with an embodiment.

Referring first to FIG. 9A, the cam 220 is shown to be in a stable unlocked position. In this position, a portion of the cam 220 having a smaller radius than other portions of the cam 220 allows release of any downward force on the cone 216. Thus, there is no contact between the frictional surfaces of the cup 214 and the cone 216. In FIG. 9B, the cam 220 is rotating counterclockwise through a gradual transition region with progressively increasing radius of the cam 222, causing a downward force to be applied to the cone 216. Thus, the cone 216 is gradually brought into contact with the cup 214, causing engagement of the brake 210.

In FIG. 9C, the cam is in a stable locked position. In this position, a portion of the cam 220 having a larger radius than other portions of the cam 220 applies a downward force on the cone 216, causing the brake to be in an engaged position. In this position, the frictional surfaces of the cup 214 and the cone 216 are in contact, thus providing a braking torque. In FIG. 9D, the cam has rotated from the stable locked position, through a rapid transition region, to the stable unlocked position of FIG. 9A.

Figure 19:
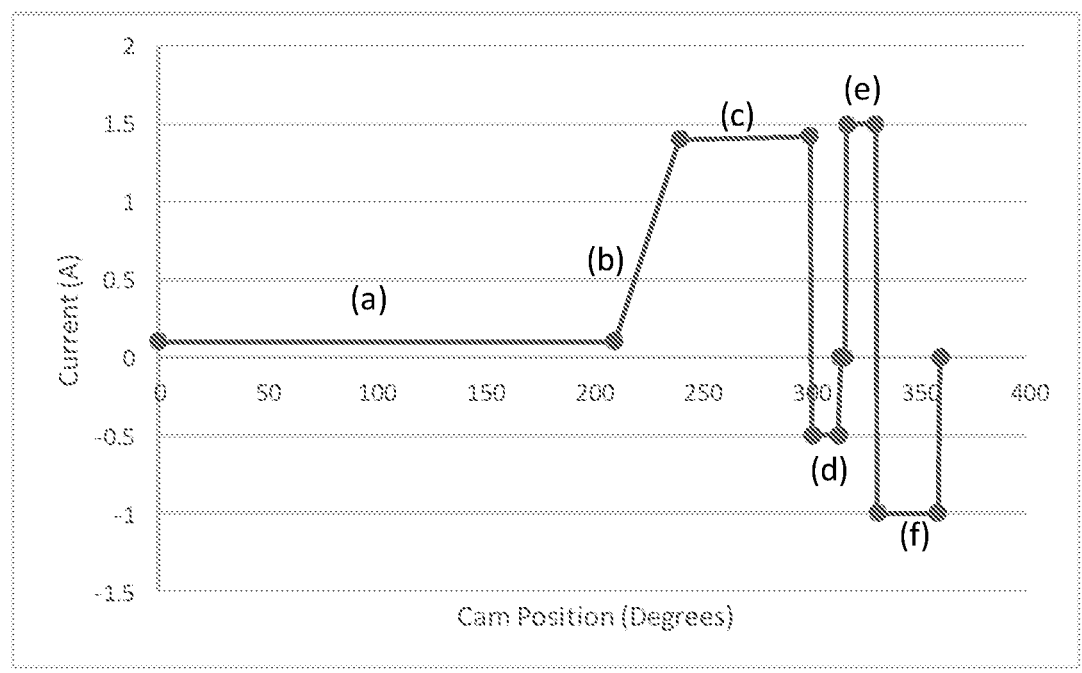
FIG. 19 illustrates a current applied to a motor as a function of a cam position.

FIG. 19 illustrates the current to the motor as a function of the position of the cam 220.

In the chart above, the motor current is proportional to the torque. Region (a) in the chart above corresponds to the cam 220 being in an unlocked position (or the stable unlocked position 184 of FIG. 8). With the lower radius resulting in lower torque, the current is proportionately low. Region (b) corresponds to the start of the gradual transition region (start of the gradual transition region 186 in FIG. 8) during which the stiffness of various components of the rotational joint and the brake is overcome, and region (c) corresponds to the gradual transition region during which the spring 218 is compressing. Region (d) corresponds to the dwell region (e.g., dwell region 182a of FIG. 8) of the stable locked region. The transition to the dwell region results in the current being negative. In one implementation region (d) is only a few degrees such as from 310-312 degrees and the current is zero. In region (e), the cam is coming out of the dwell region, but has not entered the rapid transition region, which corresponds to region (f), resulting in the negative current. Note that the brake is locked to the user at 230 degrees but fully locked at approximately 310 degrees. Stated another the user will feel resistance at 210 degrees and at 230 degrees a user will not be able to move the joint. However, if the system will continue to fully lock and have full breaking resistance at 310 degrees.

As the various components wear, the different regions of the chart above may shift. For example, the regions corresponding to the locked position or transition into locked position may decrease in duration, while the regions corresponding to unlocked position may increase.

The current profile illustrated in the example above can be used to identify the status of the cam. The current can be used to identify the locking position even as the system wears with use. The rotation can be determined as locked as soon as the preload spring comes off its hard stop. Depending on how worn the friction surfaces are, the location of this point as measured in rotation of the cam can vary greatly. A control method can use a non-constant velocity profile where the velocity is higher in the low current portion and lower in the high current portion. Using the current profile, it becomes possible to dynamically change where the system sits in the unlocked state. As the surfaces wear, the number of degrees from a predetermined point that the unlock state is defined can be increased so that the system does not need to drive in an unloaded state first. In addition to this advantage for speed, monitoring where the current begins to rapidly increase for locking allows the system to monitor wear. As this changes, the system could send an alert for service required or even fault out and not allow a case to be done if it becomes unsafe.

Referring now to FIG. 10, a perspective view of an example rotational joint 300 with an example manual actuator is illustrated. The example rotational joint 300 includes a first portion 302 and a second portion 304 that are rotatable relative to each other. In accordance with the examples described above, the first portion 302 may be coupled to an outer housing of a braking system, and the second portion 304 may be coupled to an inner housing of the braking system. Thus, the braking system can selective lock or unlock the rotation of the first portion 302 relative to the second portion 304. The example rotational joint 300 of FIG. 10 further includes rotational stops 306 which limit the range of rotation of the first portion 302 relative to the second portion 304. Rotational stops may be provided to limit the relative rotation of the first portion 302 and the second portion 304 in each direction.

The example rotational joint 300 incudes a motor-driven camshaft 340, which is illustrated more clearly in FIG. 11. The camshaft 340 includes a belt engagement wheel 342 which couples the camshaft 340 to the motor via, for example, a belt. The belt has teeth which engage corresponding teeth on the belt engagement wheel 342, thus driving the camshaft 340. The camshaft 340 is provided with a cam 344 similar to the cams described above with reference to FIGS. 7, 8 and 9A-9D.

The example rotational joint 300 of FIG. 11 further includes a manual actuator 346 coupled to the camshaft 340. The manual actuator 346 is positioned on an extension of the camshaft outside the body of the rotational joint 300, as most clearly illustrated in FIG. 10. This allows a user to manually control rotation of the camshaft 340 and the cam 344. Use of the manual actuator may be desirable when, for example, power is lost to the motor, the motor becomes disengaged from the camshaft 340, or the user otherwise wishes to override the motor.

The camshaft 340 of FIG. 10 is provided with a ratchet 348. When the camshaft 340 is motor driven, the ratchet 348 engages a counterpart coupled to the manual actuator 346. Thus, when the camshaft 340 is motor-driven, the manual actuator 346 is also motor-driven along with the camshaft 340. When the camshaft 340 is rotated using the manual actuator 346, the ratchet 348 becomes disengaged from the counterpart coupled to the manual actuator 346. Thus, when the camshaft 340 returns to being motor-driven, the ratchet 348 again engages the counterpart at the same position as it was before operation of the manual actuator 346. Disengaging the camshaft from the motor during manual actuation can be beneficial for various reasons. For example, if the motor is not back-drivable, the disengaging of the camshaft from motor can prevent the manual operation from attempting to back-drive the motor. Additionally, disengaging of the camshaft during manual operation prevents a user from manually over-speeding the motor beyond its limits.

In another example, the ratchet 348 may be reversed such that the ratchet 348 engages the counterpart only when the camshaft 340 is operated with the manual actuator 346. In this regard, the ratchet 348 is disengaged when the camshaft 340 is motor-driven. As a result, the manual actuator 346 does not rotate when the camshaft 340 is motor-driven.

FIG. 12 is a perspective view of a portion of the example rotational joint 300 of FIG. 10. As illustrated in FIG. 12, the camshaft 340 is provided with a sensor system which includes at least one sensor to allow determination of the orientation of the cam 344. In the example of FIG. 12, the camshaft is provided with a flag 352 and an optical gate 350. The optical gate 350 reads the flag 352 of the camshaft. In one example, the position of the flag 352 corresponds to the cam being in a locked position.

In other examples, the rotational joint 300 may be provided with additional sensors to determine the position of the cam relative to the position indicated by the flag 352. For example, a relative encoder may be coupled to the motor or a shaft of the motor. The relative encoder, in conjunction with the optical gate 350 can allow determination of the orientation of the cam. For example, with the flag 352 set to correspond to a stable locked position, a relative encoder can determine the position relative to the flag position and, therefore, the precise orientation of the cam.

Figure 13:
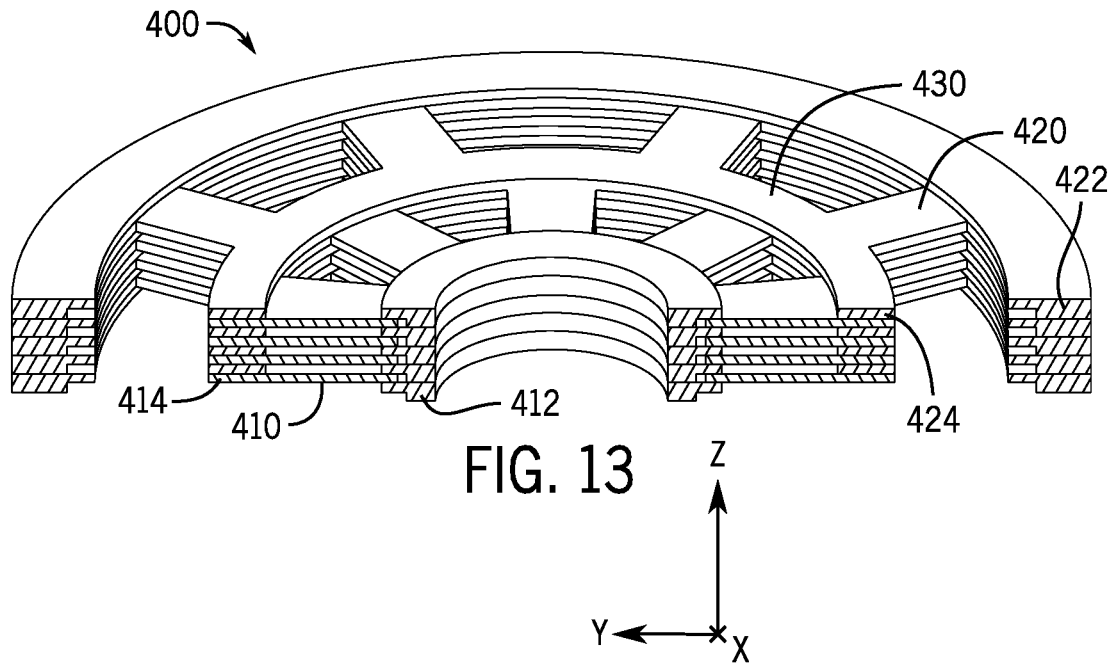
FIG. 13 is a perspective cross-sectional view of another example braking system for use with a rotational joint in accordance with an embodiment.
Figure 14:
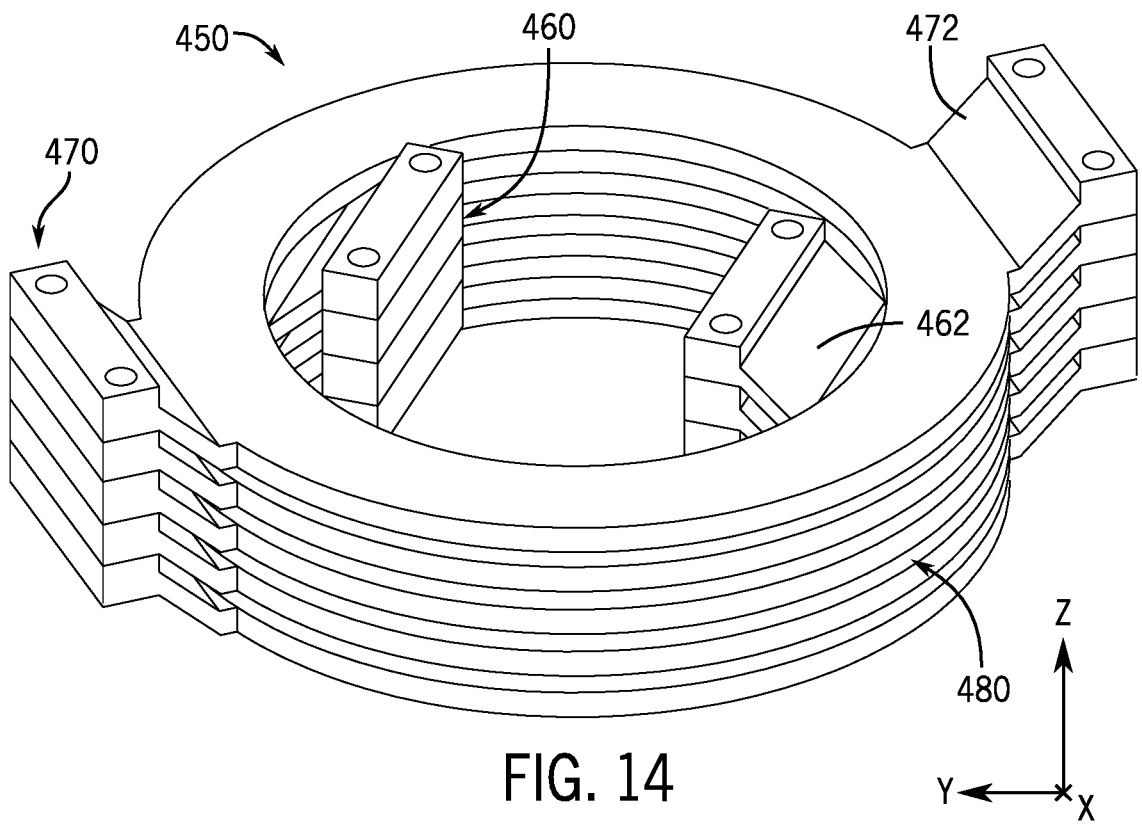
FIG. 14 is a perspective view of another example braking system for use with a rotational joint in accordance with an embodiment.
Figure 17:
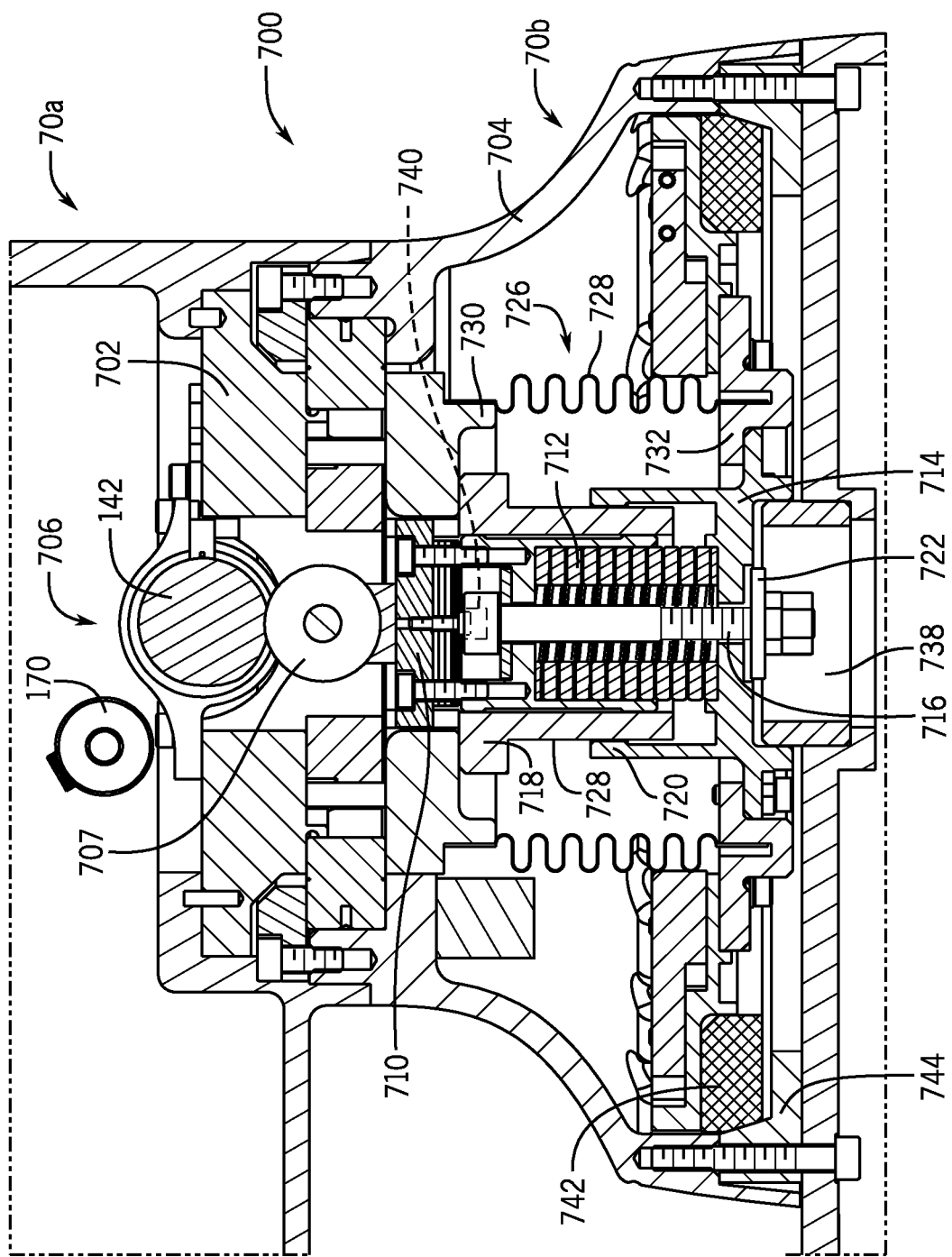
FIG. 17 is a cross-sectional view of an example rotational joint in accordance with an embodiment.
Figure 17A:
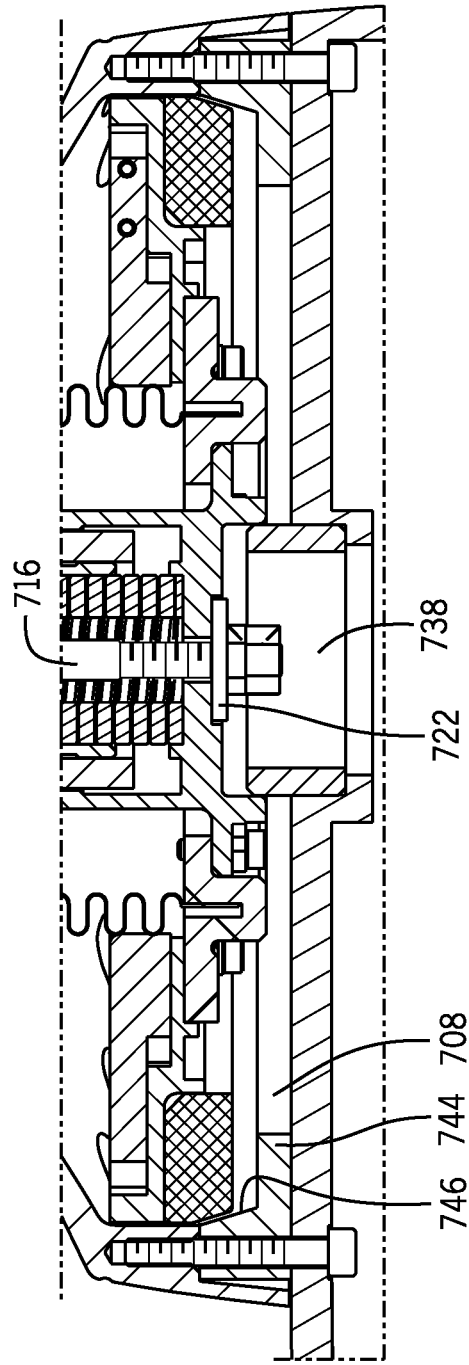
FIG. 17A is a close-up cross-sectional view of a portion of the rotational joint of FIG. 17 with a brake in an engaged position.
Figure 17B:
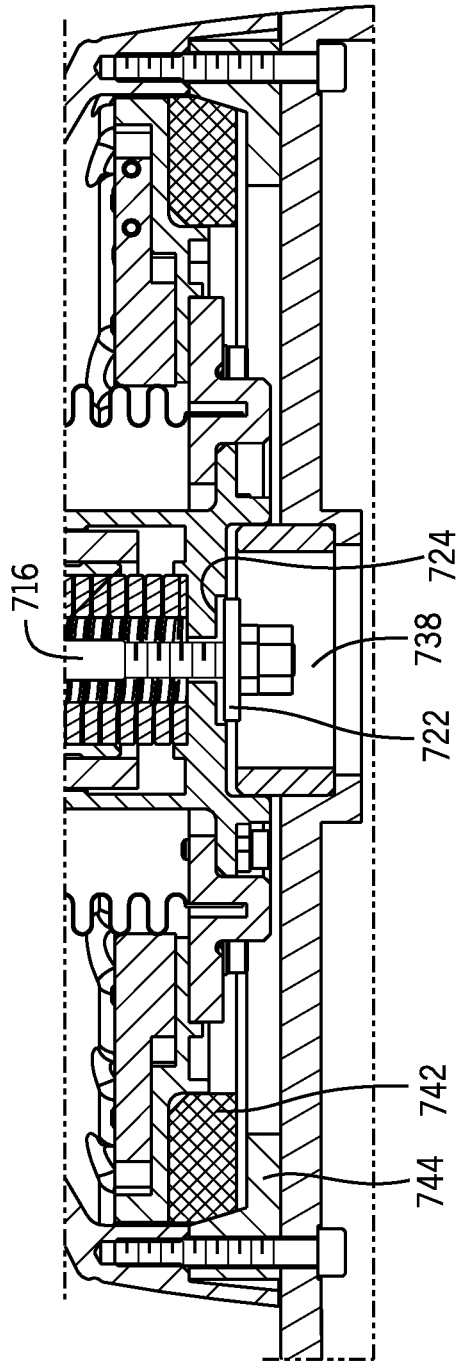
FIG. 17B is a close-up cross-sectional view of a portion of the rotational joint of FIG. 17 with a brake in the disengaged position.
Figure 18:
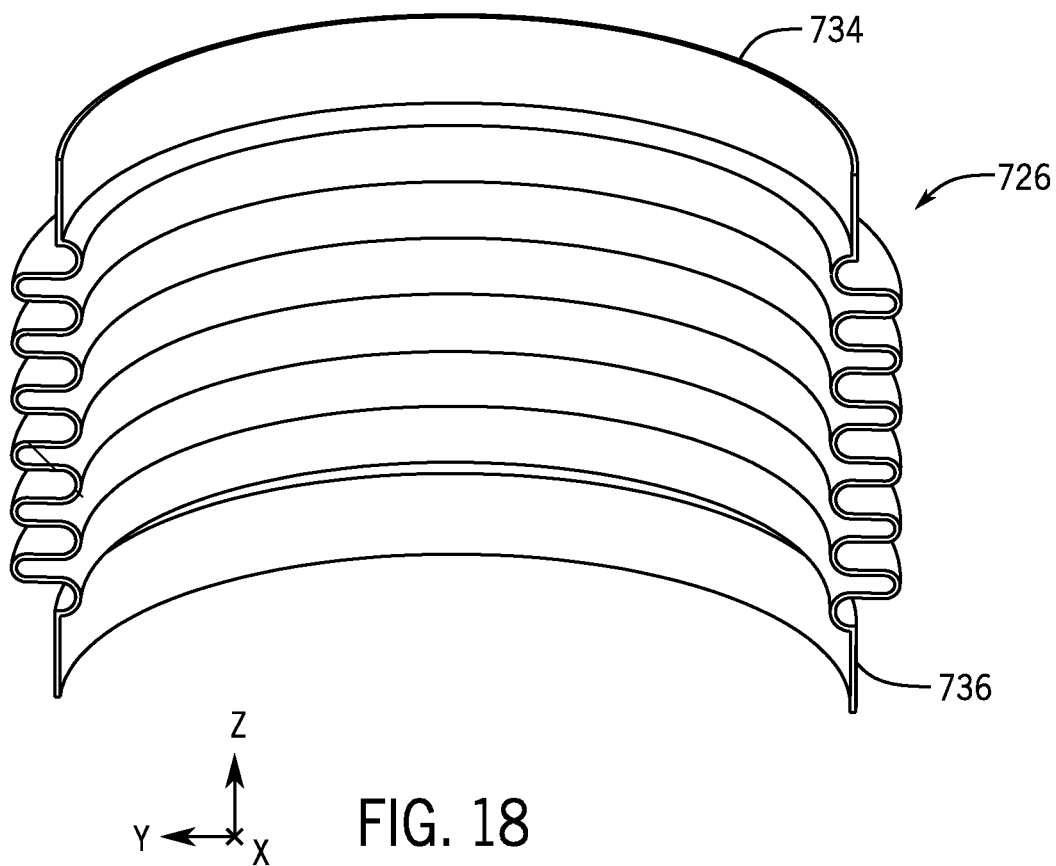
FIG. 18 is a partial view of the bellows of the rotational joint of FIG. 17.

As noted above, the various example rotational joints described herein are provided with a braking system that provides a sufficiently high locking or holding torque, infinite and results in minimal or no backlash during braking or locking. FIGS. 13 and 14 additional examples of braking systems in accordance with embodiments of the present disclosure.

Referring now to FIG. 13, a perspective cross-sectional view of an example braking system 400 for use with a rotational joint is illustrated. The example braking system 400 of FIG. 13 includes a plurality of first disc brake portions 410 having inner housing attachments 412 for coupling the first disc brake portions 410 to an inner housing. The braking system 400 further includes a plurality of second disc brake portions 420 having outer housing attachments 422 for coupling the second disc brake portions 420 to an outer housing.

The first disc brake portions 410 are provided with first frictional surfaces 414, and the second disc brake portions 420 are provided with second frictional surfaces 424. The frictional surfaces 414, 424 are interleaved circumferentially between the inner housing attachments 412 and the outer housing attachments 422. When the braking system 400 is engaged by, for example, the exertion of a downward force from a cam, the force causes the interleaved frictional surfaces 414, 424 to engage, thus causing locking of the rotation.

Referring now to FIG. 14, a perspective view of another example braking system 450 is illustrated. The example braking system 450 of FIG. 14 is similar to the braking system 400 described above with reference to FIG. 13 and includes first disc brake portions and second disc brake portions with interleaved frictional surfaces 480. In the example of FIG. 14, the braking system 450 includes inner housing attachments 460 to couple the first disc brake portions to the inner housing, and outer housing attachments 470 to couple the second disc brake portions to the outer housing.

The inner housing attachments 460 include an inner non-planar portion 462 between the inner housing and the interleaved frictional surfaces 480. The inner non-planar portion 462 includes a first end coupled to the inner housing and a second end coupled to the frictional surface, the first end and the second end being axially offset. Similarly, the outer housing attachments 470 include an outer non-planar portion 472 between the outer housing and the interleaved frictional surfaces 480. The outer non-planar portion 472 includes a first end coupled to the outer housing and a second end coupled to the frictional surface, the first end and the second end being axially offset. The axial offset between the housing and the frictional surfaces provides axial compliance (reduces axial rigidity) within the braking system.

In addition to axial compliance, various examples of braking systems for rotational joints described herein also provide torsional rigidity. In this regard, reference is again made to FIG. 5, which illustrates the use of bellows positioned around at least a portion of the brake system 130. In this regard, a bellows assembly 160 is positioned circumferentially around the brake 150. In one example the bellows assembly 160 is formed of stainless steel and is bonded to the portions of the rotational joint 100. As noted above, the bellows assembly provides torsional rigidity during the engagement of the brake. In this regard, various examples of the bellows assembly 160 provide a torsional rigidity of between about 90,000 Nm/radian and about 110,000 Nm/radian. While providing torsional rigidity, the bellows assembly 160 has low axial rigidity, thus allowing axial compliance, requiring little actuation force from the cam move the bellows assembly 160.

Referring to the example of FIG. 5, the various components illustrated in the rotational joint 100 are mounted to the outer housing 110, to the inner housing 120, and to various other components using bolted connections. The bolts used for such connections are pre-loaded sufficiently to prevent any backlash during engagement of the brake 150. Additionally, a pre-loaded cross roller bearing 199 is provided in the rotational joint 100. The cross roller bearing 199 further reduces backlash during engagement of the brake 150 to stop rotational movement between the outer housing 110 and the inner housing 120. The preloaded cross roller bearing 199 prevents the rotational joint 100 from shifting in other directions when the brake 150 is engaged.

Various examples of rotational joints are described herein. In one example, the rotational joint is a revolute joint. In this regard, the revolute joint has a single degree of freedom, namely rotation about a single axis.

FIGS. 15A and 15B are top views of the example catheter-based procedure system of FIG. 1 with the positioning system in different configurations. FIGS. 15A and 15B illustrate an example catheter-based procedure system 500 with a patient table 518, a robotic drive 524 and a positioning system 522. As noted above, the positioning system 522 may be moved out of the way (along with the robotic drive 524) to allow for the patient to be placed on the patient table 518. In this regard, the rotational joints described herein allow the positioning system 522 to be transitioned between a right-handed configuration (FIG. 15A) and a left-handed configuration (FIG. 15B). Thus, the rotational joints allow the positioning system 522 to be manipulated to any of variety of positions to allow movement of the patient to and from the patient table.

In many cases, the configuration of the system 500 in a right-handed configuration of FIG. 15A may be desirable. In this regard, in the right-handed configuration of FIG. 15A, much of the system is clear of the patient, allowing the user to operate the system without interference from the system itself. For example, in the left-handed configuration of FIG. 15B, much of the positioning system 522 is in a space between the robotic drive and the patient, restricting vision and operation of the system 500 by the operator. In the right-handed configuration, most or all of the positioning system is out of the way of the patient and the robotic drive.

As noted above with reference to FIG. 4, the second arm segment 76 includes a 4-bar linkage which can allow limited vertical movement of third rotational joint 78 relative to the second rotational joint 74. FIGS. 16A and 16B illustrate operation of a system 600 with an example 4-bar linkage. FIGS. 16A and 16B illustrate a system 600 similar to the various systems described above. In this regard, the system 600 includes a patient table 618 having a positioning system 622 mounted thereon and supporting a robotic drive 624. The positioning system 622 is similar to the various positioning systems described above and includes various rotational joints 670, 674, 678 and arm segments coupled to the rotational joints. One of the arm segments illustrated in FIGS. 16A and 16B is a linkage 676 to allow limited vertical movement of the robotic drive, illustrated in the figures with the cover removed. As illustrated in FIGS. 16A and 16B, the linkage 676 allows the robotic drive to be moved between a raised position (FIG. 16A) and a lowered position (FIG. 16B). In this regard, the raised position of FIG. 16A may be desired during, for example, moving a patient on to or off of the patient table 618. The raised position may also be desirable, for example, during mounting or removing of the robotic drive from the positioning system. The lowered position of FIG. 16B may be desired during a medical procedure to move the robotic drive closer to the patient.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

Clause 1. A rotational joint assembly for robotic medical system, comprising at least one arm segment; and a rotational joint provided at one end of the arm segment, the rotational joint to allow the arm segment to rotate about a rotational axis, the rotational joint including a brake to lock rotation of the arm segment at the rotational joint; and an actuator to selectively engage or disengage the brake, the actuator including a cam having two stable regions separated by two transition regions, the two stable regions including a first stable region corresponding to engagement of the brake and a second stable region corresponding to disengagement of the brake.

Clause 2. The rotational joint assembly of Clause 1, wherein the brake comprises a cup having a conical inner perimeter; and a cone for receiving the conical inner perimeter of the cup when the brake is engaged, wherein engaging of the brake includes moving the conical inner perimeter of the cup into contact with the cone.

Clause 3. The rotational joint assembly of Clause 2, wherein the conical inner perimeter of the cup has a cone angle of between about 15 degrees and about 30 degrees.

Clause 4. The rotational joint assembly of Clause 3, wherein the conical inner perimeter of the cup has a cone angle of about 17 degrees.

Clause 5. The rotational joint assembly of any of Clause 1, wherein the brake comprises a plurality of first disc brake portions coupled to an inner housing and a plurality of second disc brake portions coupled to an outer housing, wherein the inner housing rotates relative to the outer housing during rotation of the arm segment about the rotational joint.

Clause 6. The rotational joint assembly of Clause 5, wherein frictional surfaces of the first disc brake portions and corresponding frictional surfaces of the second disc brake portions are interleaved circumferentially between the outer housing and the inner housing.

Clause 7. The rotational joint assembly of Clause 6, wherein the first disc brake portions include an inner non-planar portion between the inner housing and the corresponding frictional surface, wherein the inner non-planar portion includes a first end coupled to the inner housing and a second end coupled to the frictional surface, and wherein the first end of the inner non-planar portion and the second end of the inner non-planar portion are axially offset.

Clause 8. The rotational joint assembly of Clause 6 or 7, wherein the second disc brake portions include an outer non-planar portion between the outer housing and the corresponding frictional surface, wherein the outer non-planar portion includes a first end coupled to the outer housing and a second end coupled to the corresponding frictional surface, and wherein the first end of the outer non-planar portion and the second end of the outer non-planar portion are axially offset.

Clause 9. The rotational joint assembly of any of Clauses 1-8, wherein the actuator includes a spring to bias the brake against the cam to a disengaged position.

Clause 10. The rotational joint assembly of Clause 9, wherein the two stable regions of the cam include the first stable region corresponding to a locked position and resulting in exertion of a force causing compression of the spring to engage the brake and the second stable region corresponding to an unlocked position and resulting in absence of the force and disengagement of the brake; and wherein the two transition regions of the cam include a gradual transition region from the second stable region to the first stable region and a rapid transition region from the first stable region to the second stable region.

Clause 11. The rotational joint assembly of any of Clauses 1-10, wherein the rotational joint allows rotation of the arm segment between a left-handed position and a right-handed position.

Clause 12. The rotational joint assembly of any of Clauses 1-11, wherein the cam is positioned on a camshaft driven by a motor.

Clause 13. The rotational joint assembly of Clause 12, wherein the camshaft includes at least one sensor to allow determination of orientation of the cam.

Clause 14. The rotational joint assembly of Clause 12 or 13, wherein the camshaft is coupled to a manual actuator to allow a user to rotate the camshaft without operation of the motor.

Clause 15. The rotational joint assembly of Clause 14, wherein the camshaft includes a ratchet configured to retain a motor-driven position of the camshaft during operation of the manual actuator, the ratchet being further configured to allow the motor to engage the camshaft at the motor-driven position upon resumption of operation of the motor.

Clause 16. The rotational joint assembly of Clause 14, wherein the camshaft includes a ratchet configured to allow the manual actuator to engage the camshaft when the camshaft is not motor-driven and to disengage the camshaft when the camshaft is motor-driven.

Clause 17. The rotational joint assembly of any of Clauses 1-16, wherein the brake is configured to cause substantially zero backlash upon engagement or disengagement.

Clause 18. The rotational joint assembly of any of Clauses 1-17, wherein the brake comprises a first brake component coupled to an outer housing and a second brake component coupled to an inner housing, the inner housing being rotatable relative to the outer housing about a rotational axis, wherein the first brake component and the second brake component are selectively engageable to each other for engagement of the brake.

Clause 19. The rotational joint assembly of Clause 18, further comprising a bellows assembly positioned circumferentially around the outer housing, the bellows assembly providing torsional rigidity during engagement of the brake.

Clause 20. The rotational joint assembly of Clause 19, wherein the bellows assembly provides a torsional rigidity of between about 90,000 Nm/radian and about 110,000 Nm/radian.

Clause 21. The rotational joint assembly of any of Clauses 1-20, wherein the rotational joint is a revolute joint.

Clause 22. The rotational joint assembly of any of Clauses 1-21, wherein the brake is a gear-less brake with a continuous braking surface.

Clause 23. A robotic medical system, comprising a brake to lock movement of at least a portion of the robotic medical system; and an actuator to selectively engage or disengage the brake, the actuator including a cam having two stable regions separated by two transition regions, the two stable regions including a first stable region corresponding to engagement of the brake and a second stable region corresponding to disengagement of the brake.

Clause 24. The robotic medical system of Clause 23, wherein the two stable regions of the cam include the first stable region corresponding to a locked position resulting in exertion of a force causing engagement of the brake and the second stable region corresponding to an unlocked position resulting in absence of the force and disengagement of the brake; and wherein the two transition regions of the cam include a gradual transition region from the second stable region to the first stable region and a rapid transition from the first stable region to the second stable region.

Clause 25. The robotic medical system of Clause 23 or 24, wherein the brake comprises a cup having a conical inner perimeter; and a cone for receiving the conical inner perimeter of the cup when the brake is engaged, wherein engaging of the brake includes moving the conical inner perimeter of the cup into contact with the cone.

Clause 26. The robotic medical system of Clause 23 or 24, wherein the brake comprises a plurality of first disc brake portions coupled to an inner housing and a plurality of second disc brake portions coupled to an outer housing, wherein the inner housing rotates relative to the outer housing during rotation of an arm segment about a rotational joint.

Clause 27. A rotational joint assembly for robotic medical system comprising at least one arm segment and a rotational joint provided at one end of the arm segment, the rotational joint to allow the arm segment to rotate about a rotational axis, the rotational joint including a brake to lock rotation of the arm segment at the joint and an actuator to selectively engage or disengage the brake, wherein the brake includes a cup having a conical inner perimeter and a cone for receiving the conical inner perimeter of the cup when the brake is engaged, wherein engaging of the brake includes moving the conical inner perimeter of the cup into contact with the cone.

Clause 28. The rotational joint assembly of Clause 27, wherein the conical inner perimeter of the cup has a cone angle of between about 15 degrees and about 30 degrees.

Clause 29. The rotational joint assembly of Clause 28, wherein the conical inner perimeter of the cup has a cone angle of about 17 degrees.

I claim:

1. A rotational joint assembly for a robotic medical system, the rotational joint assembly, comprising:
    at least one arm segment; and
    a rotational joint provided at one end of the at least one arm segment, the rotational joint configured to allow the at least one arm segment to rotate about a rotational axis, the rotational joint comprising,
        a brake to lock rotation of the at least one arm segment at the rotational joint, the brake including,
            a cup having a conical inner perimeter; and
            a cone for receiving the conical inner perimeter of the cup when the brake is engaged, and
        an actuator to selectively engage or disengage the brake, the actuator comprising a cam having two stable regions separated by two transition regions, the two stable regions comprising a first stable region corresponding to engagement of the brake and a second stable region corresponding to disengagement of the brake,
    wherein engaging of the brake includes moving the conical inner perimeter of the cup into contact with the cone.

2. The rotational joint assembly of claim 1, wherein the conical inner perimeter of the cup has a cone angle of between about 15 degrees and about 30 degrees.

3. The rotational joint assembly of claim 2, wherein the conical inner perimeter of the cup has a cone angle of about 17 degrees.

4. The rotational joint assembly of claim 1, wherein the brake comprises a plurality of first disc brake portions coupled to an inner housing and a plurality of second disc brake portions coupled to an outer housing, wherein the inner housing rotates relative to the outer housing during rotation of the at least one arm segment about the rotational joint.

5. The rotational joint assembly of claim 4, wherein frictional surfaces of the first disc brake portions and corresponding frictional surfaces of the second disc brake portions are interleaved circumferentially between the inner housing and the outer housing.

6. The rotational joint assembly of claim 5, wherein the first disc brake portions include an inner non-planar portion between the inner housing and the corresponding frictional surface,
    wherein the inner non-planar portion comprises a first end coupled to the inner housing and a second end coupled to the frictional surface;
    wherein the first end of the inner non-planar portion and the second end of the inner non-planar portion are axially offset.

7. The rotational joint assembly of claim 5, wherein the second disc brake portions include an outer non-planar portion between the outer housing and the corresponding frictional surface; and
    wherein the outer non-planar portion comprises a first end coupled to the outer housing and a second end coupled to the corresponding frictional surface;
    wherein the first end of the outer non-planar portion and the second end of the outer non-planar portion are axially offset.

8. The rotational joint assembly of claim 1, wherein the actuator comprises a spring to bias the brake against the cam to a disengaged position.

9. The rotational joint assembly of claim 8,
    wherein the two stable regions of the cam include:
        the first stable region corresponding to a locked position and resulting in exertion of a force causing compression of the spring to engage the brake; and
        the second stable region corresponding to an unlocked position and resulting in absence of the force and disengagement of the brake;
    wherein the two transition regions of the cam include:
        a gradual transition region from the second stable region to the first stable region; and
        a rapid transition region from the first stable region to the second stable region.

10. The rotational joint assembly of claim 1, wherein the rotational joint allows rotation of the arm segment between a left-handed position and a right-handed position.

11. The rotational joint assembly of claim 1, wherein the cam is positioned on a camshaft driven by a motor.

12. The rotational joint assembly of claim 11, wherein the camshaft comprises at least one sensor to allow determination of orientation of the cam.

13. The rotational joint assembly of claim 11, wherein the camshaft is coupled to a manual actuator to allow a user to rotate the camshaft without operation of the motor.

14. The rotational joint assembly of claim 13, wherein the camshaft comprises a ratchet configured to retain a motor-driven position of the camshaft during operation of the manual actuator, the ratchet being further configured to allow the motor to engage the camshaft at the motor-driven position upon resumption of operation of the motor.

15. The rotational joint assembly of claim 13, wherein the camshaft comprises a ratchet configured to allow the manual actuator to engage the camshaft when the camshaft is not motor-driven and to disengage the camshaft when the camshaft is motor-driven.

16. The rotational joint assembly of claim 1, further comprising a bellows enclosing at least substantially an entirety of the brake, the bellows providing torsional rigidity during engagement of the brake to cause substantially zero backlash upon engagement or disengagement.

17. The rotational joint assembly of claim 1, wherein the brake comprises:
 a first brake component coupled to an outer housing; and
 a second brake component coupled to an inner housing, the inner housing being rotatable relative to the outer housing about a rotational axis,
 wherein the first brake component and the second brake component are selectively engageable to each other for engagement of the brake.

18. A robotic medical system comprising:
 a brake to lock movement of at least a portion of the robotic medical system, the brake including,
  a cup having a conical inner perimeter, and
  a cone for receiving the conical inner perimeter of the cup when the brake is engaged; and
 an actuator to selectively engage or disengage the brake, the actuator including a cam having two stable regions separated by two transition regions, the two stable regions comprising a first stable region corresponding to engagement of the brake and a second stable region corresponding to disengagement of the brake,
 wherein the actuator is configured to engage the brake by moving the conical inner perimeter of the cup into contact with the cone.

19. A rotational joint assembly for a robotic medical system, the rotational joint assembly comprising:
 at least one arm segment; and
 a rotational joint provided at one end of the at least one arm segment, the rotational joint to allow the at least one arm segment to rotate about a rotational axis, the rotational joint comprising,
  a brake to lock rotation of at least one the arm segment at the joint, and
  an actuator including a cam configured to selectively engage or disengage the brake,
 wherein the brake comprises,
  a cup having a conical inner perimeter, and
  a cone for receiving the conical inner perimeter of the cup when the brake is engaged,
 wherein the actuator is configured to engage the brake by rotating the cam such that the conical inner perimeter of the cup contacts the cone.

\* \* \* \* \*